United States Patent [19]
O'Mahony et al.

[11] Patent Number: 6,034,121
[45] Date of Patent: Mar. 7, 2000

[54] CHROMONE FUNGICIDES

[75] Inventors: Mary Josephine O'Mahony; Peter John West, both of Cambridge; Jacqueline Anne MacRitchie, Saffron Walden, all of United Kingdom; Stephen David Lindell, Frankfurt am Main, Germany; Peter Millward, Cambridge, United Kingdom

[73] Assignee: Agrevo UK Limited, United Kingdom

[21] Appl. No.: 09/051,135

[22] Filed: Apr. 1, 1998

[30] Foreign Application Priority Data

| Oct. 13, 1995 | [GB] | United Kingdom | 9521023 |
|---|---|---|---|
| Nov. 25, 1995 | [GB] | United Kingdom | 9524152 |
| Dec. 14, 1995 | [GB] | United Kingdom | 9525514 |
| Dec. 14, 1995 | [GB] | United Kingdom | 9525524 |
| Dec. 14, 1995 | [GB] | United Kingdom | 9525525 |
| Dec. 14, 1995 | [GB] | United Kingdom | 9525526 |

[51] Int. Cl.⁷ .................. A01N 43/16; C07D 311/18; C07D 311/22; C07D 311/54; C07D 311/56

[52] U.S. Cl. .................. 514/456; 549/284; 549/285; 549/288; 549/400; 549/401; 504/292

[58] Field of Search .................. 549/284, 285, 549/288, 400, 401; 504/292; 514/456, 457

[56] References Cited

U.S. PATENT DOCUMENTS

| 3,141,893 | 7/1964 | Pfister et al. | 260/343.2 |
|---|---|---|---|
| 3,801,597 | 4/1974 | Makisumi | 260/332.2 |
| 4,065,574 | 12/1977 | Moon | 424/283 |
| 4,230,850 | 10/1980 | Briet et al. | 544/151 |
| 4,841,076 | 6/1989 | Kitagawa et al. | 549/401 |
| 5,382,572 | 1/1995 | Afonso et al. | 514/82 |
| 5,412,104 | 5/1995 | Afonso et al. | 548/525 |
| 5,510,375 | 4/1996 | Domagala et al. | 514/457 |
| 5,681,968 | 10/1997 | Alvarado et al. | 549/285 |

FOREIGN PATENT DOCUMENTS

| 0694257 | 1/1996 | European Pat. Off. |
|---|---|---|
| 2321 | 2/1964 | France . |
| 1225658 | 9/1966 | Germany . |
| 7818575 | 2/1978 | Japan . |
| 5-331009 | 12/1993 | Japan . |

OTHER PUBLICATIONS

Chemical Abstracts, vol. 102, No. 1, 1985, Columbus, Ohio, U.S., Abstract No. 214470b, L. Heimark, et al., "A Stable Isotope Assay For Phenprocoumon", p. 3, Column 2.

Biomed Mass Spectrom., vol. 12, No. 2, 1985, Seattle, pp. 67–71.

Chemical Abstracts, vol. 89, No. 28, 1978, Columbus, Ohio, U.S., Abstract No. 43430v, p. 637, Column 2.

*Primary Examiner*—Laura L. Stockton
*Attorney, Agent, or Firm*—Ostrolenk, Faber, Gerb & Soffen, LLP

[57] ABSTRACT

Compounds of the formula

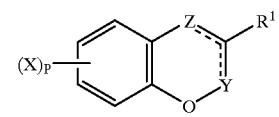

where one of Z and Y is CO and the other is C—W—R² and the dotted line indicates a double bond is present where necessary to meet valency requirements, W is O, S(O)$_n$, N(R³), N(R³)(R⁴), N(R³)O or ON(R³); R¹ is hydrogen, or an optionally substituted alkyl, alkenyl, alkynyl, cycloalkyl, phenyl or heterocyclyl group; R², R³ and R⁴, which may be the same or different, are as defined above for R¹, or are acyl, or R² and R³ or R² and R⁴ or R³ and R⁴ together with the nitrogen or oxygen to which they are attached form an optionally substituted ring which may contain other hetero atoms; each X, which may be the same as or different from any other X, is halogen, CN, NO₂, SF₅, B(OH)₂, triakylsilyl or a group E, OE or S(O)$_n$E where E is a group as defined hereinbefore for R² or is optionally substituted amino; or two adjacent groups X together with the atoms to which they are attached form an optionally substituted carbocyclic or heterocyclic ring; n is 0, 1 or 2; and p is 0 to 4 have fungicidal activity. Many of the compounds are novel.

15 Claims, No Drawings

CHROMONE FUNGICIDES

This application is a 371 of PCT/GB96/02491 filed Oct. 11, 1996.

FIELD OF THE INVENTION

This invention relates to new bicyclic heterocyclic compounds useful as fungicides.

PRIOR ART

Certain chromones and their isomeric coumarins have been disclosed as having fungicidal properties.

U.S. Pat. No. 4,065,574 discloses fungicidal chromones which are substituted in the 2-position by various groups including hydroxy.

EP 567828 discloses fungicidal phenylacrylate derivatives in which a coumarinyloxymethyl or chromonyloxymethyl croup is attached to the 2-position of the phenyl group. In this patent, the phenylacrylate part of the molecule would be considered as the toxophore.

U.S. Pat. No. 4,380,649 discloses coumarin substituted in the 4 position by an isophoronyloxy group and no other substituent.

DESCRIPTION OF THE INVENTION

We have now found that certain chromones and coumarins have particularly valuable fungicidal properties In one aspect, the invention provides the use as fungicides of compounds of formula I

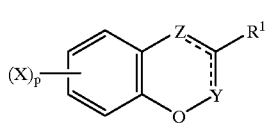

(I)

where
one of Z and Y is CO and the other is C—W—R$^2$;
and the dotted line indicates a double bond is present in the appropriate position to meet valency requirements;
W is O, S(O)$_n$, N(R$^3$), N(R$^3$)N(R$^4$), N(R$^3$)O or ON(R$^3$);
R$^1$ is hydrogen, or an optionally substituted alkyl, alkenyl, alkynyl, cycloalkyl, phenyl or heterocyclyl group;
R$^2$, R$^3$ and R$^4$, which may be the same or different, are as defined above for R$^1$, or are acyl, or
R$^2$ and R$^3$ or R$^2$ and R$^4$ or R$^3$ and R$^4$ together with the nitrogen or oxygen to which they are attached form an optionally substituted ring which may contain other hetero atoms;
each X, which may be the same as or different from any other X, is halogen, CN, NO$_2$, SF$_5$, B(OH)$_2$, trialkylsilyl or a group E, OE or S(O)$_n$E where E is a group as defined hereinbefore for R$^2$ or is optionally substituted amino; or two adjacent groups X together with the atoms to which they are attached form an optionally substituted carbocyclic or heterocyclic ring;
n is 0, 1 or 2; and
p is 0 to 4
with the proviso:
a) when W is O, R$^2$ is not o-substituted benzyl,
b) when p is 0, R$^1$ is not hydrogen, and
c) when Z is CO and W is O, R$^2$ is not hydrogen.

Many of the compounds are novel and the invention thus includes compounds of formula I where one of Z and Y is CO and the other is C—W—R$^2$
and the dotted line indicates a double bond is present where necessary to meet valency requirements
W is O, S(O)$_n$, N(R$^3$), N(R$^3$)N(R$^4$), N(R$^3$)O or ON(R$^3$);
R$^1$ is an optionally substituted alkyl, alkenyl, alkynyl, cycloalkyl or phenyl group;
R$^2$, R$^3$ and R$^4$, which may be the same or different, are as defined above for R$^1$, or are acyl or optionally substituted heterocyclyl, or
R$^2$ and R$^3$ or R$^2$ and R$^4$ or R$^3$ and R$^4$ together with the nitrogen or oxygen to which they are attached form an optionally substituted ring which may contain other hetero atoms;
each X, which may be the same as or different from any other X, is halogen, CN, NO$_2$, SF$_5$, B(OH)$_2$, trialkylsilyl or a group E, OE or S(O)$_n$E where E is a group as defined hereinbefore for R or is optionally substituted amino; or two adjacent groups X together with the atoms to which they are attached form an optionally substituted carbocyclic or heterocyclic ring;
n is 0, 1 or 2; and
p is 1 or 2 with one X group being in the 6-position, with the proviso:
a) when Z is CO and WR$^2$ is methoxy, R$^1$ is not 1-methylbenzyl or 1,1-dimethylallyl,
b) when Z is CO and WR$^2$ is NMe$_2$, two X groups cannot form a benzo ring fused to the 5 and 6 positions, and
c) when Y is CO, then W is O, in which case R$^2$ is not methyl, nor mono- or di-alkylaminaminoalkyl.

Any alkyl group present in the molecule is preferably of 1 to 10 carbon atoms, especially of 1 to 7 carbon atoms, and particularly of 1 to 5 carbon atoms, and may be straight or branched.

Any alkenyl or alkynyl group present in the molecule, may be straight or branched and is preferably of 2 to 7 carbon atoms, for example allyl, vinyl or propargyl.

Any cycloalkyl group present in the molecule is preferably of 3 to 7 carbon atoms, especially cyclopropyl, cyclopentyl, or cyclohexyl.

Substituents, when present on any alkyl, alkenyl, alkynyl or cycloalkyl moiety may for example be halogen, cyano, tralkylsilyl, optionally substituted alkoxy, optionally substituted alkylthio, hydroxy, nitro, optionally substituted amino, acyl, acyloxy, optionally substituted phenyl, optionally substituted heterocyclyl optionally substituted phenylthio, optionally substituted phenoxy, optionally substituted heterocyclyloxy, optionally substituted heterocyclylthio or oxidised derivatives of thio-containing groups. Cycloalkyl groups may also be substituted by alkyl.

The term heterocyclyl includes both heteroaryl groups as described below and non-aromatic heterocyclyl groups.

Heteroaryl groups are generally 5- or 6-membered rings containing up to 4 hetero atoms selected from nitrogen, oxygen and sulfur, optionally fused to a benzene ring. Examples of heteroaryl groups are those derived from thiophene, furan, pyrrole, thiazole, oxazole, imidazole, isothiazole, isoxazole, pyrazole, 1,3,4-oxadiazole, 1,3,4-thiadiazole, 1,2,4-oxadiazole, 1,2,4-thiadiazole, 1,2,4-triazole, 1,2,3-triazole, tetrazole, benzo[b]thiophene, benzo[b]furan, indole, benzo[c]thiophene, benzo[c]furan, isoindole, benzoxazole, benzothiazole, benzimidazole, benzisoxazole, benzisothiazole, indazole, benzothiadiazole, benzotriazole, dibenzofuran, dibenzothiophene, carbazole, pyridine, pyrazine, pyrimidine, pyridazine, 1,3,5-triazine, 1,2,4-triazine, 1,2,4,5-tetrazine, quinoline, isoquinoline, quinoxaline, quinazoline, cinnoline, 1,8-naphthyridine, 1,5-naphthyridine, 1,6-naphthyridine, 1,7-naphthyridine, phthalazine, pyridopyrimidine, purine or pteridine.

Non-aromatic heterocyclyl groups are generally 3, 5, 6 or 7-membered rings containing up to 3 hetero atoms from nitrogen, oxygen and sulfur, for example oxiranyl, thiiranyl, thiazolinyl, dioxolanyl, 1,3-benzoxazinyl, 1,3-benzothiazinyl, morpholino, pyrazolinyl, sulfolanyl, dihydroquinazolinyl, piperidinyl, phthalimido; tetrahydrofuranyl, tetrahydropyranyl, pyrrolidinyl, indolinyl, 2-oxopyrrolidino, 2-oxobenzoxazolin-3-yl or tetrahydroazepinyl.

Substituents when present on any phenyl or heterocyclyl group may for example be halogen, CN, $NO_2$, $SF_5$, $B(OH)_2$, trialkylsilyl, acyl, O-acyl or a group E, OE or $S(O)_nE$ as defined hereinbefore for $R^2$ or is optionally substituted amino; or two adjacent groups on the ring together with the atoms to which they are attached form a carbocyclic or heterocyclic ring, which may be similarly substituted.

The term acyl includes the residue of sulfur and phosphorus-containing acids as well as carboxylic acids. Examples of acyl groups are thus $—COR^5$, $—COOR^5$, $—CLNR^5R^6$, $—CON(R^5)OR^6$, $—COONR^5R^6$, $—CON(R^5)NR^6R^7$, $—COSR^5$, $—CSSR^5$, $—S(O)_qR^5$, $—S(O)_2OR^5$, $—S(O)_qNR^5R^6$, $—P(=L)(OR^5)(OR^6)$ or $—COOR^5$, where $R^5$, $R^6$ and $R^7$, which may be the same or different, are hydrogen, optionally substituted alkyl, optionally substituted cycloalkyl, optionally substituted cycloalkenyl, optionally substituted alkenyl, optionally substituted alkynyl, optionally substituted phenyl or optionally substituted heterocyclyl, or $R^5$ and $R^6$, or $R^6$ and $R^7$, together with the atom(s) to which they are attached can form a ring, q is 1 or 2 and L is O or S.

Amino groups may be substituted for example by one or two optionally substituted alkyl or acyl groups, or two substituents can form a ring, preferably a 5- to 7-membered ring, which may be substituted and may contain other hetero atoms, for example morpholine.

p is generally 1 or 2.

X is preferably halogen; alkyl, e.g. $C_{1-5}$-alkyl, especially methyl; alkenyl, e.g. $C_{2-4}$-alkenyl; alkynyl, e.g. $C_{2-4}$-alkynyl, optionally substituted by trialkylsilyl; alkoxy, e.g. $C_{1-5}$-alkoxy, especially methoxy; haloalkoxy, e.g. halo-$C_{1-5}$-alkoxy; alkenyloxy, e.g. $C_{2-4}$-alkenyloxy; alkynyloxy, e.g. $C_{2-4}$-alkynyloxy; cycloalkyloxy, e.g. $C_{3-6}$-cycloalkyloxy; or alkylthio, e.g. $C_{1-5}$-alkylthio, especially methylthio; or two X groups together form a methylenedioxy group.

W is preferably O, S, SO, $SO_2$, NH or N-alkyl, e.g. N-methyl.

$R^1$ is preferably $C_{3-6}$-cycloalkyl; $C_{2-4}$-alkenyl; phenyl or alkyl, e.g. $C_{1-6}$-alkyl, optionally substituted by hydroxy, hydroxyimino, $C_{1-6}$-alkoxyimino or $C_{1-6}$alkanoyloxy.

$R^2$ is preferably $C_{3-6}$-cycloalkyl; phenyl; or alkyl, e.g. $C_{1-6}$-alkyl, optionally substituted by $C_{1-6}$-alkoxy, $C_{3-6}$-cycloalkyl or phenyl.

In the compounds of the invention, X is preferably in the 6 position or the 6 and 8-positions on the ring.

The invention also includes the compounds disclosed in the Examples except those where $WR^2$ is OH, which are synthesised as intermediates.

The compounds of the invention have activity as fungicides, especially against fungal diseases of plants, e.g. mildews and particularly cereal powdery mildew (*Erysiphe graminis*), vine powdery mildew (*Uncinula necator*), vine downy mildew (*Plasmopara viticola*), rice blast (*Pyricularia oryzae*), cereal eyespot (*Pseudocercosporella herpotrichoides*), rice sheath blight (*Pellicularia sasakii*), grey mould (*Botrytis cinerea*), damping off (*Rhizoctonia solani*), wheat brown rust (*Puccinia recondita*), late tomato or potato blight (*Phytophthora infestans*), apple scab (*Venturia inaequalis*), glume blotch (*Leptosphaeria nodorum*). Other fungi against which the compounds may be active include other powdery mildews, other rusts, and general pathogens of Deuteromycete, Ascomycete, Phycomycete and Basidomycete origin.

The invention thus also provides a method of combating fungi at a locus infested or liable to be infested therewith, which comprises applying to the locus a compound of formula I.

The invention also provides an agricultural composition comprising a compound of formula I in admixture with an agriculturally acceptable diluent or carrier.

The composition of the invention may of course include more than one compound of the invention.

In addition, the composition can comprise one or more additional active ingredients, for example compounds known to possess plant-growth regulant, herbicidal, fungicidal, insecticidal or acaricidal properties. Alternatively, the compound of the invention can be used in sequence with the other active ingredient.

The diluent or carrier in the composition of the invention can be a solid or a liquid optionally in association with a surface-active agent, for example a dispersing agent, emulsifying agent or wetting agent. Suitable surface-active agents include anionic compounds such as a carboxylate, for example a metal carboxylate of a long chain fatty acid; an N-acylsarcosinate; mono- or di-esters of phosphoric acid with fatty alcohol ethoxylates or salts of such esters; fatty alcohol sulfates such as sodium dodecyl sulfate, sodium octadecyl sulfate or sodium cetyl sulfate; ethoxylated fatty alcohol sulfates; ethoxylated alkylphenol sulfates; lignin sulfonates; petroleum sulfonates; alkyl-aryl sulfonates such as alkyl-benzene sulfonates or lower alkylnaphthalene sulfonates, e.g. butyl-naphthalene sulfonate; salts of sulfonated naphthalene-formaldehyde condensates; salts of sulfonated phenol-formaldehyde condensates; or more complex sulfonates such as the amide sulfonates, e.g. the sulfonated condensation product of oleic acid and N-methyl taurine or the dialkyl sulfosuccinates, e.g. the sodium sulfonate of dioctyl succinate. Nonionic agents include condensation products of fatty acid esters, fatty alcohols, fatty acid amides or fatty-alkyl- or alkenyl-substituted phenols with ethylene oxide, fatty esters of polyhydric alcohol ethers, e.g. sorbitan fatty acid esters, condensation products of such esters with ethylene oxide, e.g. polyoxyethylene sorbitan fatty acid esters, block copolymers of ethylene oxide and propylene oxide, acetylenic glycols such as 2,4,7,9-tetramethyl-5-decyne-4,7-diol, or ethoxylated acetylenic glycols.

Examples of a cationic surface-active agent include, for instance, an aliphatic mono-, di-, or polyamine as an acetate, naphthenate or oleate; an oxygen-containing amine such as an amine oxide or polyoxyethylene alkylamine; an amide-linked amine prepared by the condensation of a carboxylic acid with a di- or polyamine; or a quaternary ammonium salt.

The compositions of the invention can take any form known in the art for the formulation of agrochemicals, for example, a solution, a dispersion, an aqueous emulsion, a dusting powder, a seed dressing, a fumigant, a smoke, a dispersible powder, an emulsifiable concentrate or granules. Moreover it can be in a suitable form for direct application or as a concentrate or primary composition which requires dilution with a suitable quantity of water or other diluent before application.

An emulsifiable concentrate comprises a compound of the invention dissolved in a water-immiscible solvent which is formed into an emulsion with water in the presence of an emulsifying agent.

A dusting powder comprises a compound of the invention intimately mixed and ground with a solid pulverulent diluent, for example, kaolin.

A granular solid comprises a compound of the invention associated with similar diluents to those which may be employed in dusting powders, but the mixture is granulated by known methods. Alternatively it comprises the active ingredient absorbed or adsorbed on a pre-granular diluent, for example, Fuller's earth, attapulgite or limestone grit.

Wettable powders, granules or grains usually comprise the active ingredient in admixture with a suitable surfactant and an inert powder diluent such as china clay.

Another suitable concentrate is a flowable suspension concentrate which is formed by grinding the compound with water or other liquid, a wetting agent and a suspending agent.

The concentration of the active ingredient in the composition of the present invention, as applied to plants is preferably within the range of 0.0001 to 1.0 per cent by weight, especially 0.0001 to 0.01 per cent by weight. In a primary composition, the amount of active ingredient can vary widely and can be, for example, from 5 to 95 per cent by weight of the composition.

In the method of the invention, the compound is generally applied to seeds, plants or their habitat. Thus, the compound can be applied directly to the soil before, at or after drilling so that the presence of active compound in the soil can control the growth of fungi which may attack seeds. When the soil is treated directly the active compound can be applied in any manner which allows it to be intimately mixed with the soil such as by spraying, by broadcasting a solid form of granules, or by applying the active ingredient at the same time as drilling by inserting it in the same drill as the seeds. A suitable application rate is within the range of from 5 to 1000 g per hectare, more preferably from 10 to 500 g per hectare.

Alternatively, the active compound can be applied directly to the plant by, for example, spraying or dusting either at the time when the fungus has begun to appear on the plant or before the appearance of fungus as a protective measure. In both such cases, the preferred mode of application is by foliar spraying. It is generally important to obtain good control of fungi in the early stages of plant growth as this is the time when the plant can be most severely damaged. The spray or dust can conveniently contain a pre- or post-emergence herbicide if this is thought necessary. Sometimes, it is practicable to treat the roots of a plant before or during planting, for example, by dipping the roots in a suitable liquid or solid composition. When the active compound is applied directly to the plant a suitable rate of application is from 0.025 to 5 kg per hectare, preferably from 0.05 to 1 kg per hectare.

The novel compounds of the invention can be prepared in various ways in known manner. Typical methods are shown in the following reaction schemes Synthesis route to compounds of formula I where Y is CO and Z is $CWR^2$

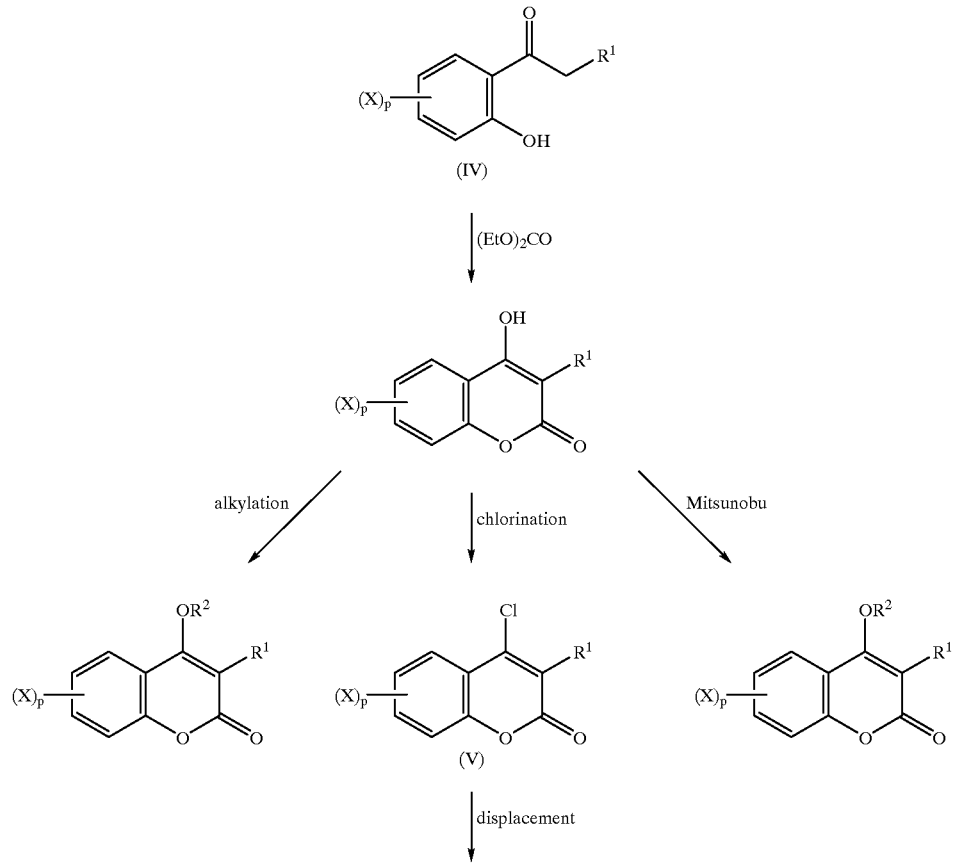

-continued
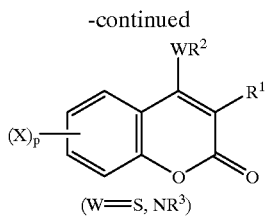
Synthesis route to compounds of formula I where Z is CO and Y is CWR$^2$
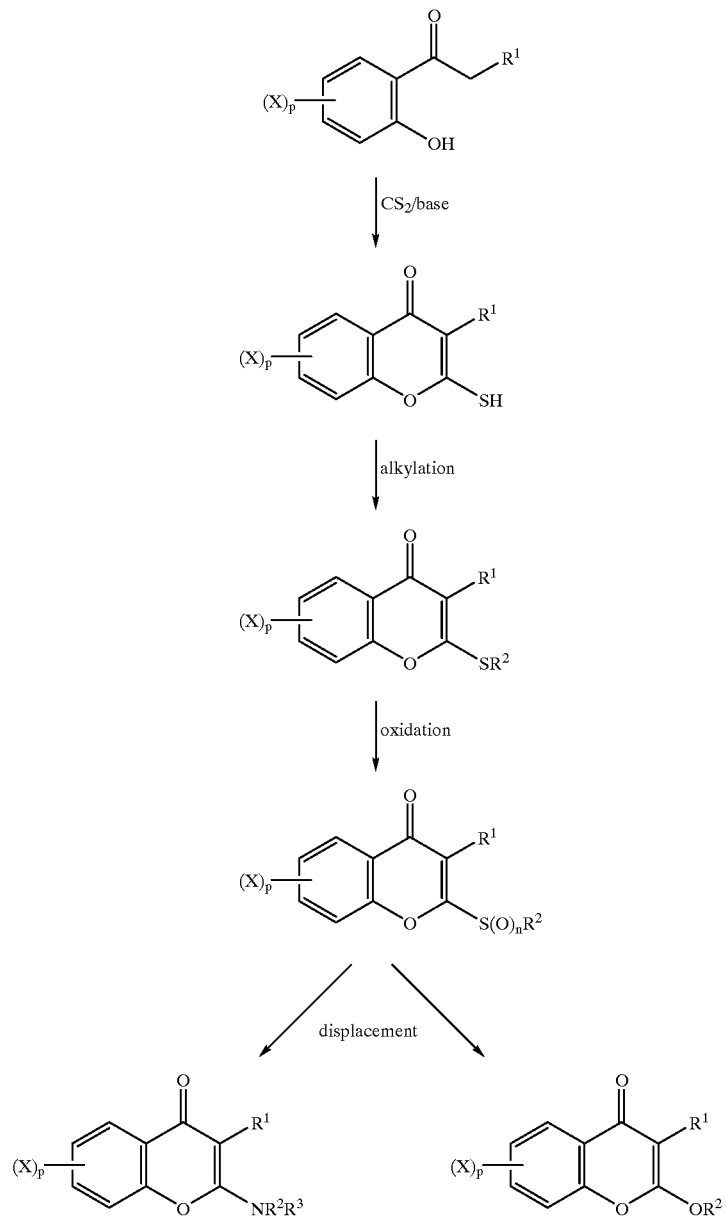
The compounds of formula I where Y is CO and Z is COH may be prepared by reaction of a phenol of formula II

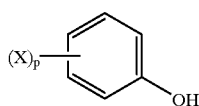

(II)

where X and p are as defined hereinbefore with a malonic acid derivative of the formula III

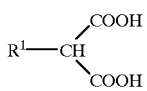

(III)

where $R^1$ is as defined hereinbefore, to give the desired compound.

The reaction may be effected as described for example in J. Org. Chem., 1960, 25, 677, by heating the reactants in the presence of anhydrous zinc chloride and phosphorus oxychloride. If excess reagents are used, then compounds of formula V can be obtained by this procedure.

Alternatively, the compound of formula I where Y is CO and Z is COH can be as prepared from the phenols of formula II by acylation using an acyl chloride of formula $R^1CH_2COCl$ to give the corresponding phenyl ester, followed by rearrangement to the corresponding o-acylphenol of formula IV.

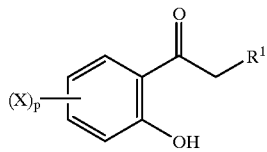

(IV)

usually by heating in the presence of aluminium trichloride. The boron trifluoride complex of the compound of formula IV is then formed by reaction with boron trifluoride etherate, which is reacted with dichloromethylenedimethylammonium chloride to form the corresponding dimethylaminochloromethylene compound. This is then cyclised in acetonitrile/water to give the desired compound of formula I, where Y is CO and Z is COH.

Preferably, however, the cyclisation of compound IV to the compound of formula I, where Y is CO and Z is COH, is carried out using diethyl carbonate and sodium hydride.

Compounds of formula I, where Y is CO and Z is $COR^2$, where $R^2$ is other than hydrogen can be prepared from this compound by reaction with a compound of formula $R^2Q$, where Q is a leaving group, e.g. halogen or p-toluenesulfonyloxy, in the presence of a base or by reaction with an alcohol of formula $R^2OH$ under Mitsunobu conditions ($PPh_3$, DEAD).

The compounds of formula II and III are either known or can be prepared by methods analogous to those known for preparing analogous known compounds.

Compounds of formula I, where Y is CO and Z is C—W—$R^2$, where W is other than O can be prepared by reaction of a compound of formula V

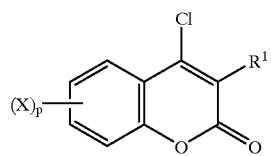

(V)

with an appropriate nucleophile, i.e. $R^2SH$, $R^2R^3NH$, $R^2R^4NN(R^3)H$, $R^2ON(R^3)H$ or $R^2R^3NOH$, in the presence of a base, where $R^2$–$R^4$ are as defined hereinbefore.

Compounds of formula I, where Y is CO and Z is C—W—$R^2$, where W is $N(R^3)$, can also be prepared by reaction of compounds of formula I, where $WR^2$ is OH, with an amine of formula $HNR^2R^3$, for example as described in Synthesis 1987, 308.

Compounds of formula V can be prepared by reaction of the corresponding compound of formula I where $WR^2$ is OH with phosphorus oxychloride (Monatsh Chem 1986, 117, 1305–23).

Compounds of formula I, where Y is CO and Z is C—W—$R^2$ and W is S, can be oxidised to give compounds where W is SO or $SO_2$.

Compounds of formula I, where Z is CO and Y is C—SH, can be prepared by cyclising the compound of formula IV with carbon disulfide in the presence of a base.

This compound can then be alkylated, acylated etc., in the presence of a base in known manner, to give the compound where $R^2$ is other than hydrogen.

The alkylated compound may then be oxidised in suitable manner to give a compound where Z is CO and Y is $CS(O)_nR^2$, where n is 1 or 2. Compounds of formula I, where Z is CO and Y is CH—W—$R^2$ and W is other than S, can be prepared from the compound where W is SO or $SO_2$, with an appropriate nucleophile, i.e. $R^2OH$, $R^2R^3NH$, $R^2R^4NN(R^3)H$, $R^2ON(R^3)H$ or $R^2R^3NOH$, in the presence of a base, where $R^2$–$R^4$ are as defined hereinbefore, for example using methods disclosed in J. Het. Chem., 1981, 18, 679.

Alternatively, the compounds may be obtained by methods similar to those disclosed in Chemistry and Industry 1980, 116; J. Chem. Soc. Chem. Com. 1 1981, 282 and J. Org. Chem. 1992, 57, 6502.

Other methods will be apparent to the chemist skilled in the art as will be the methods for preparing starting materials and intermediates. The Examples also make apparent various methods of preparing compounds of the invention as well as starting materials and intermediates.

The invention is illustrated in the following Examples, which illustrates the preparation of compounds of the invention as well as hydroxy intermediates. Structures of isolated novel compounds were confirmed by NMR and/or other appropriate analyses.

EXAMPLE 1

A solution of 2-acetyl-4-bromophenol (20 g) and carbon disulfide (7 ml) in toluene (400 ml) was added dropwise to a suspension of potassium tert.-butoxide (31.4 g) in toluene (500 ml) at 10° C. The mixture was stirred at room temperature for 72 hours. Glacial acetic acid (35 ml) was added and the mixture evaporated under reduced pressure. The residue was treated with water (200 ml) and glacial acetic acid (20 ml) to precipitate an oily solid. Light petroleum (b.p. 40–60° C.) was added and the mixture stirred for one hour, filtered and the solid was collected and washed with light petroleum to give 6-bromo-2-mercapto-4H-1-benzopyran-4-one, m.p. 230° C. (compound 1)

In a similar manner, there was obtained 6-bromo-3-ethyl-2-mercapto-4H-1-benzopyran-4-one, (compound 1a)

EXAMPLE 2

A solution of compound 1a (1.8 g) in acetone (50 ml) was stirred with potassium carbonate (0.92 g) and methyl iodide (0.8 ml) added. The mixture was stirred for 15 minutes, filtered and evaporated under reduced pressure. The residue was dissolved in ethyl acetate and the solution washed with water, dried, filtered and evaporated and the residue triturated with light petroleum (b.p. 40–60° C.) to give 6-bromo-3-ethyl-2-methylthio-4H-1-benzopyran-4-one, m.p. 142–3° C. (compound 2)

EXAMPLE 3

A solution of compound 2 (1.44 g) in dichloromethane (10 ml) was cooled to 0° C. and a dry dichloromethane solution of meta-chloroperbenzoic acid (20 ml) (prepared by 1.66 g of 50% pure material dissolved in dichloromethane and dried over magnesium sulfate) was added slowly. The mixture was stirred at 0° C. overnight, washed with aqueous sodium carbonate, dried and evaporated. The solid obtained was triturated with ethyl acetate, filtered and the solid collected to give 6-bromo-3-ethyl-2-methylsulfinyl-4H-1-benzopyran-4-one, m.p. 169–70° C. (compound 3).

EXAMPLE 4

In a similar manner to example 3 but using double the stochiometric amount of meta-chloroperbenzoic acid, 6-methoxy-2-methylthio-3-propyl-4H-1-benzopyran-4-one gave 6-methoxy-2-methylsulfonyl-3-propyl-4H-1-benzopyran-4-one, m.p. 1 53–155° C. (compound 4)

EXAMPLE 5

A solution of compound 3 (0.3 g) in acetonitrile was treated with isopropylamine (1 ml). The mixture was stirred overnight at room temperature, evaporated under reduced pressure and the residue purified by silica gel chromatography followed by trituration with light petroleum (b.p. 40–60° C.) to give 6-bromo-3-ethyl-2-isopropylamino-4H-1-benzopyran-4-one, m.p. 189–90° C. (compound 5)

EXAMPLE 6

Dimethylamine was bubbled through a solution of compound 3 (0.3 g) in acetonitrile (5 ml) for 10 minutes. The mixture was stirred overnight at room temperature, solvent was evaporated under reduced pressure and the residue purified by silica gel chromatography to give 6-bromo-2-dimethylamino-3-ethyl-4H-1-benzopyran-4-one, m.p. 107–8° C. (compound 6)

EXAMPLE 7

Dimethylamine was bubbled through a solution of compound 4 (0.4 g) in acetonitrile (20 ml) for 10 minutes. The solvent was evaporated under reduced pressure and the residue dissolved in dichloromethane. The extract was washed with brine, dried, filtered and evaporated to give 2-dimethylamino-6-methoxy-3-propyl-4H-1-benzopyran-4-one, as a brown oil (compound 7)

EXAMPLE 8

Meta-chloroperbenzoic acid (50.72 g of 50% pure material) was dissolved in dichloromethane (250 ml), the water separated off and the organic phase dried over magnesium sulfate. This solution was then added to a solution of 6-methyl-2-methythio-4H-1-benzopyran-4-one (compound 110—see later) (10.13 g) in dichloromethane (50 ml) with cooling and the mixture stirred at room temperature overnight. Sodium methoxide (20.11 g) in methanol (250 ml) was added and the mixture stirred at room temperature for 1 hour and then evaporated under reduced pressure. Water (500 ml) was added and the mixture extracted with ethyl acetate. The extract was washed with water, dried and evaporated under reduced pressure. The product was re-crystallised from methanol to give 2-methoxy-6-methyl-4H-1-benzopyran-4-one, m.p. 166–7° C. (compound 8)

EXAMPLE 9

Sodium methoxide (0.08 g) was added to a solution of compound 4 (0.4 g) in dry methanol (8 ml). The mixture was stirred for 5 minutes. The solvent was evaporated under reduced pressure and water was added. The solid material was collected and dried to give 2,6-dimethoxy-3-propyl-4H-1-benzopyran-4-one, m.p. 78–80° C. (compound 9)

EXAMPLE 10

N-bromosuccinimide (3.97 g) was added with stirring to a solution of compound 8 (3.85 g) in dichloromethane (50 ml) and the mixture stirred for 3 hours. Water (200 ml) was added and the mixture extracted with dichloromethane. The extract was washed with water, dried over magnesium sulfate and evaporated under reduced pressure. The residue was recrystallised from toluene to give 3-bromo-2-methoxy-6-methyl-4H-1-benzopyran-4-one, m.p. 158–66° C. (compound 10)

EXAMPLE 11

A mixture of compound 10 (0.51 g), phenylboronic acid (0.25 g), tetrakis(triphenylphosphine)palladium(0) (0.11 g), potassium carbonate (1.05 g) toluene (6 ml), ethanol (2 ml) and water (4 ml) was heated under reflux overnight, cooled, added to water and extracted with ethyl acetate. The extract was washed with water, dried, evaporated and the residue was purified by silica gel column chromatography, followed by trituration with light petroleum (b.p. 40–60° C.) to give 2-methoxy-6-methyl-3-phenyl-4H-1-benzopyran-4-one, m.p. 112–5° C. (compound 11)

EXAMPLE 12

Phenylacetyl chloride (9.4 g) was added dropwise to 4-bromophenol (10 g) in pyridine, and the reaction mixture was stirred at room temperature for 1 hour then evaporated to dryness under reduced pressure. The residue was taken up in ethyl acetate, washed with water, dried over magnesium sulfate, filtered and evaporated under reduced pressure to give 4-bromophenyl phenylacetate.

Aluminium trichloride (5.5 g) was added portionwise with stirring to this compound (8 g), and the reaction mixture was heated to 160° C. for 1 hour. The hot, viscous oil produced was poured into ice/concentrated hydrochloric acid (100 ml), and the aqueous phase was extracted with dichloromethane. The organics were washed with brine (×2), dried over magnesium sulfate, filtered and evaporated to give 5'-bromo-2'-hydroxy-2-phenylacetophenone.

To this product (3.2 g) in diethyl ether (30 ml) was added boron trifluoride etherate (1.6 ml), and the reaction mixture was stirred for 1 hour, after which the diethyl ether was removed in vacuo to give the boron trifluoride complex.

To this product (3.2 g) in dichloroethane (45 ml) was added dichloromethylene-dimethylammonium chloride (1.8 g). The reaction mixture was heated to 80° C. for 2 hours, and then cooled, with the solvent being removed in vacuo to give the boron trifluoride complex of 5'-bromo-2-[chloro (dimethylamino)methylene]-2'-hydroxy-2-phenylacetophenone.

To this product was added acetonitrile/water (5:1), and the reaction mixture was heated to 50° C. for 1 hour. The solvent was then removed in vacuo, and the solid material was triturated with diethyl ether, then filtered off and air dried to give 6-bromo-2-dimethylamino-3-phenyl-4H-1-benzopyran-4-one, m.p. 118–120° C. (compound 12)

EXAMPLE 13

Pentanoyl chloride (12.7 g) was added dropwise to 3-bromophenol (9.0 g) in pyridine (50 ml), and the reaction mixture was stirred at room temperature for 1 hour. Work-up as described in Example 12 gave 3-bromophenyl pentanoate.

Aluminium trichloride (12.74 g) was added portionwise with stirring to this product (16.5 g) and the reaction mixture was heated to 160° C. for 1 hour. The hot, viscous oil produced was poured into ice/concentrated hydrochloric acid (100 ml), and the aqueous phase was extracted with dichloromethane, washed with brine (×2), dried over magnesium sulfate, filtered and evaporated to give 1-(4-bromo-2-hydroxy-phenyl)-1-pentanone.

To this product (6.5 g) in diethyl ether (30 ml) was added boron trifluoride etherate (3.75 g), and the reaction mixture was stirred for 1 hour, after which the diethyl ether was removed under reduced pressure to give the boron trifluoride complex of 1-(4-bromo-2-hydroxyphenyl)-1-pentanone.

To this product (8.0 g) in dichloroethane (50 ml) was added dichloromethylene-dimethylammonium chloride (4.4 g). The reaction mixture was heated to 80° C. for 2 hours, and then cooled, with the solvent being removed under reduced pressure to give the boron trifluoride complex of 1-(4-bromo-2-hydroxyphenyl)-2-[chloro-(dimethylamino) methylene]-1-pentanone.

To this product (7.0 g) was added acetonitrile/water (5:1, 60 ml), and the reaction mixture was heated to 50° C. for 1 hour. The solvent was then removed under reduced pressure, and the solid material was triturated with diethyl ether, then filtered off and air dried to give 7-bromo-4-hydroxy-3-propyl-2H-benzopyran-2-one, m.p. 138–40° C. (compound 13)

In a similar manner there was obtained 6-bromo-4-hydroxy-3-propyl-2H-benzopyran-2-one, m.p. 216–8° C. (compound 13a)

EXAMPLE 14

A mixture of compound 13 (0.5 g), propyl bromide (0.23 g) and potassium carbonate (0.22 g) in acetone (5 ml) was refluxed overnight, after which the solvent was removed under reduced pressure. The residue was taken up in diethyl ether, washed with water, brine, dried over magnesium sulfate, filtered and evaporated to give 7-bromo-4-propoxy-3-propyl-2H-benzopyran-2-one, m.p. 73–5° C. (compound 14)

EXAMPLE 15

1-Butanethiol (0.39 ml) was added dropwise to a solution of sodium (0.08 g) in ethanol (3 ml). The solution was stirred for ½ hour and then added slowly to a refluxing solution of 6-bromo-4-chloro-3-propyl-2H-1-benzopyran-2-one (1 g) in ethanol (4 ml). The mixture was heated under reflux for 4½ hours, filtered hot through kieselguhr and the filtrate allowed to cool. The precipitate was purified by silica gel column chromatography to give 6-bromo-4-butylthio-3-propyl-2H-1-benzopyran-2-one, m.p. 62–4° (compound 15)

Preparation of the starting material

Tributylamine (12 ml) was added dropwise to a stirred mixture of compound 13a (5 g) and phosphoryl chloride (80.2 ml) in toluene (50 ml). The mixture was heated at 100–10° C. overnight. It was then poured into ice-water and extracted with ethyl acetate. The extracts were washed with water and brine, dried and evaporated. The residue was purified by silica gel column chromatography to give 6-bromo-4-chloro-3-propyl-2H-1-benzopyran-2-one, m.p. 96–7° C.

EXAMPLE 16

A solution of 6-bromo-4-chloro-3-propyl-2H-1-benzopyran-2-one (0.5 g) in dimethylformamide (2 ml) was treated with sodium diethyldithiocarbamate (0.34 g). The mixture was stirred at room temperature under nitrogen overnight and then poured into water, extracted with diethyl ether and the extract washed with brine, dried and evaporated under reduced pressure to give 6-bromo-4-diethylthiocarbamoylthio-3-propyl-2H-1-benzopyran-2-one, m.p. 135–7°. (compound 16)

EXAMPLE 17

A mixture of butylamine (3 ml) and compound 13a (0.5 g) was heated under reflux for 45 minutes. The mixture was dissolved in methanol and aqueous sodium hydroxide (0.1 mol) was added and the mixture heated under reflux for 36 hours. Further butylamine (10 ml) was added and the mixture heated for 20 hours at 100° C. in a bomb. The mixture was diluted with ethyl acetate and the extract washed with water, dried and evaporated under reduced pressure. The residue was purified by silica gel chromatography to give 6-bromo-4-butylamino-3-propyl-2H-1-benzopyran-2-one, m.p. 153–40.(compound 17)

EXAMPLE 18

A solution of 6-bromo-4-chloro-3-propyl-2H-1-benzopyran-2-one (0.4 g) and N-methylbutylamine (3 ml) in dimethylformamide (2 ml) was heated under reflux for 30 minutes and then allowed to cool overnight. Evaporation followed by column chromatography yielded 6-bromo-4-(butylmethylamino)-3-propyl-2H-1-benzopyran-2-one, as an oil. (compound 18).

EXAMPLE 19 m-Chloroperbenzoic acid (0.29 g 50% suspension in water) was added to a solution of compound 15 (0.3 g) in dichloromethane (3 ml) at 0° C. The mixture was warmed to 10° C., diluted with dichloromethane and washed with aqueous sodium bicarbonate, dried and evaporated. Trituration with light petroleum gave 6-bromo-4-butylsulfinyl-3-propyl-2H-1benzopyran-2-one, m.p. 122–3° C. (compound 19)

EXAMPLE 20

A mixture of 6-bromo-4-chloro-3-propyl-2H-1-benzopyran-2-one (0.5 g) with sodium hydride (0.8 g of 60% in oil) and 4-methoxyphenol (0.24 g) in dry dimethylformamide (5 ml) was stirred at room temperature overnight under nitrogen. The mixture was poured into dilute hydrochloric acid and extracted with diethyl ether. The extracts were washed with sodium hydroxide, brine, dried and evaporated under reduced pressure. The residue was triturated with light petroleum (b.p. 40–60° C.) to give 6-bromo-4-(4-methoxyphenoxy)-3-propyl-2H-1-benzopyran-2-one, m.p. 104–6° C. (compound 20).

In a similar manner, there was obtained 6-bromo-4-phenylthio-3-propyl-2H-1-benzopyran-2-one, m.p. 84–5° C. (compound 20a)

EXAMPLE 21

Triethylamine was added to a solution of 6-bromo-4-chloro-3-propyl-2H-1-benzopyran-2-one (0.5 g), in dry ethanol (10 ml) followed by 2-methoxyethylamine (0.16 ml). The mixture was heated at reflux under nitrogen overnight, evaporated and the residue extracted with ethyl acetate and the extract washed with dilute hydrochloric acid, brine, dried and evaporated under reduced pressure. The residue was triturated with ethanol and light petroleum (b.p. 40–60° C.) to give 6-bromo-4-(2-methoxyethylamino)-3-propyl-2H-1-benzopyran-2-one, m.p. 75–7° C. (compound 21).

EXAMPLE 22

3-methylanthranilic acid (12.5 g) was added slowly with stirring to sulfuric acid (61 ml: 7.5M) cooled to 0° C. A solution of sodium nitrite (5.7 g) in water (19 ml) was added dropwise maintaining the temperature below 5° C. The mixture was stirred for half an hour at room temperature and heated at 79–80° C. for one hour then cooled. Water was added and the mixture allowed to stand over the weekend. The mixture was filtered and the precipitate collected and washed with water. It was dissolved in ethyl acetate and the solution washed with water, stirred with barium chloride for 2 hours to remove any residual sulfuric acid, filtered, washed with water, dried and evaporated under reduced pressure to give 3-methylsalicylic acid, m.p. 160–2° C.

A solution of this compound (10.6 g) in tetrahydrofuran (60 ml) was treated with butyllithium (92 ml of 2.5 mol in hexane) which was added at a rate to maintain reflux. The mixture was heated at reflux overnight under nitrogen, cooled and poured into a mixture of 6N hydrochloric acid, ice and sodium chloride. The mixture was extracted with ethyl acetate and the extracts washed with brine, dried and evaporated under reduced pressure. The residue was triturated with light petroleum (b.p. 40–60° C.). The mixture was filtered and the filtrate evaporated under reduced pressure to give 2'-hydroxy-3'-methylvalerophenone as a brown gum.

This compound (6 g) was dissolved in diethyl carbonate (20 ml) and the solution added dropwise to a stirred suspension of sodium hydride (3.75 g of 60% in oil) in diethyl carbonate (21.5 ml). The mixture was slowly warmed to 120° C. under nitrogen for 3½ hours, cooled, poured into water, acidified to pH 1, stirred for one hour and allowed to stand overnight. The mixture was filtered and the solid washed with water and cyclohexane. The solid was dissolved in ethyl acetate and the solution washed with water, dried and evaporated under reduced pressure to give 4-hydroxy-8-methyl-3-propyl-2H-1-benzopyran-2-one, m.p. 180–2° C.(compound 22).

EXAMPLE 23

A mixture of compound 22 (1 g), potassium carbonate (0.76 g) and 1-bromobutane (0.59 ml) in dimethylformamide (5 ml) was stirred overnight under nitrogen. The solvent was evaporated under reduced pressure and the residue extracted with ethyl acetate. The extract was washed with water, dried and evaporated and the residue purified by silica gel column chromatography to give 4-butoxy-8-methyl-3-propyl-2H-1-benzopyran-2-one, m.p. 35–7° C. (compound 23)

EXAMPLE 24

A solution of 4-bromophenol (20 g) in dry pyridine (75 ml) was cooled to 0° C. and heptanoyl chloride (18.79 ml) was added dropwise. The mixture was stirred at room temperature for 2½ hours. Water (10 ml) was added to dissolve the precipitate and the mixture then evaporated under reduced pressure. The residue was dissolved in diethyl ether, washed with water, hydrochloric acid, water, aqueous saturated sodium hydrogen carbonate, water, dried and evaporated under reduced pressure to give 4-bromophenyl heptanoate.

Aluminium trichloride (22.44 g) was added portionwise to this compound (32 g) and the mixture was heated at 160° C. in an oil bath for 3½ hours. It was then cooled to room temperature, poured into ice/1M hydrochloric acid (600 ml) with stirring. Dichloromethane was added and the aqueous layer extracted with dichloromethane. The combined extracts were washed with water, dried and evaporated under reduced pressure to give 4-bromo-2-heptanoylphenol as a brown oil. In a similar manner to Example 22, this compound was treated with sodium hydride in diethyl carbonate to give 6-bromo-4-hydroxy-3-pentyl-2H-1-benzopyran-2-one, m.p. 176–8° C. (compound 24)

This was treated with 1-bromobutane in a similar manner to Example 23 to give 6-bromo-4-butoxy-3-pentyl-2H-1-benzopyran-2-one, m.p. 56–8° C. (compound 24a).

EXAMPLE 25

A cooled (10° C.) stirred solution of 4-bromophenol (3 g) and triethylamine (2.5 ml) in dichloromethane (100 ml) was treated with 4-chlorophenylacetyl chloride (3.3 g) in dichloromethane (50 ml). The mixture was stirred at room temperature overnight. The solution was washed with water, dried over magnesium sulfate, filtered and evaporated under reduced pressure. The residue was purified by silica gel chromatography to give 4-bromophenyl 4-chlorophenylacetate.

A solution of this compound (5.8 g) and aluminium trichloride (3.6 g) in o-dichlorobenzene was stirred and heated at 130° C. for 2 hour, cooled to room temperature and poured carefully into cold dilute hydrochloric acid (500 ml). The mixture was extracted into dichloromethane and the organic layer separated, dried over magnesium sulfate, filtered and evaporated under reduced pressure. The residue was purified by silica gel chromatography to yield 5'-bromo-2'-hydroxy-2-(4-chlorophenyl)acetophenone as a white solid.

A solution of this compound (5.1 g) in dry toluene (100 ml) was treated with carbon disulfide (1.1 ml). The mixture was cooled to approximately 10° C. and potassium t-butoxide (6 g) was added maintaining temperature. The mixture was stirred overnight at room temperature. The mixture was acidified with glacial acetic acid and evaporated to dryness under reduced pressure. The residue was treated with water (100 ml) and stirred for 1 hour. The precipitate was filtered and dried over phosphorus pentoxide to yield 6-bromo-2-mercapto-3-(4-chlorophenyl)-4H-1-benzopyran-4-one. (compound 25)

This compound (2.1 g) in dry acetone (100 ml) was stirred at room temperature with potassium carbonate (0.5 g) for 15 minutes. Methyl iodide (0.5 ml) was added and stirring continued for 2 hours before evaporation to dryness. The residue was partitioned between dichloromethane and water. The organic phase was separated, dried over magnesium sulfate, filtered and evaporated under reduced pressure. The residue was crystallised from toluene to give 6-bromo-2-methylthio-3-(4-chlorophenyl)-4H-1-benzopyran-4-one, m.p. 205–6° C.

EXAMPLE 26

Pentanoyl chloride (39.8 g) in dichloromethane (50 ml) was added slowly to a solution of p-cresol (32.4 g) and triethylamine (36.4 g) in dichloromethane (250 ml) with ice cooling. After 1 hour the reaction mixture was washed with brine, dried over magnesium sulfate, filtered and evaporated under reduced pressure to give 4-methylphenyl pentanoate.

Aluminium trichloride (45 g) was added slowly to a solution of the previous compound (43 g) in o-dichlorobenzene (100 ml). The mixture was heated to 165° C. for 2½ hours then allowed to cool overnight. The mixture was poured on to ice (600 ml) containing concentrated hydrochloric acid (40 ml) and stirred until the ice melted. The mixture was extracted with dichloromethane and the extract washed with brine, dried over magnesium sulfate and evaporated under reduced pressure to give 2'-hydroxy-4'-methylvalerophenone as a solution in dichlorobenzene.

The previous solution (84 g≡20 g of compound) was added slowly at room temperature to a suspension of sodium hydride (12.5 g of 60% dispersion in oil) in diethyl carbonate (125 ml). The mixture was heated at reflux for 3 hours, cooled to room temperature and poured slowly on to ice/water. The organic layer was separated and the aqueous layer washed with dichloromethane. The aqueous phase was acidified with concentrated hydrochloric acid and the precipitate collected by filtration to give 4-hydroxy-6-methyl-3-propyl-2H-benzopyran-2-one, m.p. 184–6° C. (compound 26).

This product was treated with 1-bromobutane in a similar manner to Example 23, to give 4-butoxy-6-methyl-3-propyl-2H-benzopyran-2-one, m.p. 49° C. (compound 26a)

EXAMPLE 27

A solution of titanium trichloride (7.71 g) in water (50 ml) was added to a solution of ethyl (5-bromo-2-thienyl) glyoxylate (5.0 g) and 5-bromo-2-hydroxybenzaldehyde (4.36 g) in dry acetic acid (50 ml) with stirring at 4° C. and the mixture was stirred for 1½ hours. It was extracted with ethyl acetate and the extract was washed with water, brine, dried over magnesium sulfate and evaporated under reduced pressure. The residue was dissolved in toluene and p-toluenesulfonic acid (2.5 g) was added and the mixture heated under reflux for 2½ hours. It was allowed to stand at room temperature overnight and evaporated under reduced pressure. The residue was purified by silica gel column chromatography to give 6-bromo-3-(5-bromo-2-thienyl)-4-hydroxy-2H-1-benzopyran-2-one, m.p. 234–6° C. (compound 27)

EXAMPLE 28

To a solution of compound 27 (0.25 g) in dimethylformamide (5 ml) was added potassium carbonate (0.2 g) and butyl bromide (0.11 ml) and the mixture heated at 75° C. for 2½ hours. Butyl bromide (0.11 ml) was added and the mixture allowed to stand at room temperature for 2 days. The mixture was added to water (20 ml) and extracted with ethyl acetate. The extract was dried and evaporated under reduced pressure and the residue purified by silica gel column chromatography to give 6-bromo-3-(5-bromo-2-thienyl)-4-butoxy-2H-1-benzopyran-2-one, m.p. 104–5° C. (compound 28)

EXAMPLE 29

Butyl bromide (0.05 ml) was added with stirring to a mixture of a solution of 6-bromo-4-hydroxy-3-phenyl-2H-1-benzopyran-2-one (80 mg) (Synthesis 1993, 99), in dry dimethylformamide (0.5 ml) and potassium carbonate (70 mg). The mixture was stirred for 48 hours and water (5 ml) was added. The mixture was extracted with diethyl ether and the extract washed with water, dried and evaporated under reduced pressure. The residue was washed with water and dried to give 6-bromo-4-butoxy-3-phenyl-2H-1-benzopyran-2-one, m.p. 87–9° C. (compound 29)

EXAMPLE 30

A solution of diethyl azodicarboxylate (0.83 ml, 5.3 mmol) in dry THF (3.5 ml) was added slowly to a solution of compound 13a (1 g), triphenylphosphine (1.39 g) and benzyl alcohol (10.55 ml) in tetrahydrofuran (14 ml) at room temperature uder nitrogen. The mixture was stirred for 4 hours, evaporated under reduced pressure and the residue purified by silica gel column chromatography to give 4-benzyloxy-6-bromo-3-propyl-2H-1-benzopyran-2-one, mp. 121–3° C. (compound 30a) and 2-benzyloxy-6-bromo-3-propyl-4H-1-benzopyran-4-one, mp. 50–2° C. (compound 30b)

The following compounds of the invention and intermediates were prepared in an analogous manner to one of the previous examples:

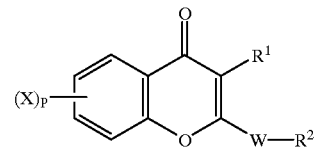

| Cpd | WR² | (X)ₚ | R¹ | m.p. (° C.) |
|---|---|---|---|---|
| 41 | NMe₂ | 6-Cl | Pr | 88–90 |
| 42 | SEt | 6-Br | Pr | 109–10 |
| 43 | SOEt | 6-Br | Pr | 130–1 |
| 44 | NHBu | 6-Br | Pr | 136–8 |

-continued

[Structure: chromone with (X)p on benzene ring, R¹ at 3-position, W–R² at 2-position, 4-oxo]

| Cpd | WR² | (X)p | R¹ | m.p. (° C.) |
|---|---|---|---|---|
| 45 | N(Me)Bu | 6-Br | Pr | oil |
| 46 | NMe₂ | 6-Br | H | 163–4 |
| 47 | SBu | 6-Br | Pr | 44 |
| 48 | OBu | 6-Br | Pr | 57–8 |
| 49 | NMe₂ | 6-Br | Pr | 93–5 |
| 50 | OMe | 6-Br | Pr | 125–6 |
| 51 | SPr | 6-Br | Pr | 70–2 |
| 52 | S-pentyl | 6-Br | Pr | 40–2 |
| 53 | S-allyl | 6-Br | Pr | 83–4 |
| 54 | SMe | 6-Br | Pr | 124–5 |
| 55 | SOMe | 6-Br | Pr | 148–9 |
| 56 | N-morpholinyl | 6-Br | Pr | 139–41 |
| 57 | NHMe | 6-Br | Pr | 167–70 |
| 58 | N(Me)Pr | 6-Br | Pr | oil |
| 59 | OBu | 6-Br | pentyl | 56–8 |
| 60 | OBu | 6-Br | Et | 109–11 |
| 61 | OBu | 6-Br | Bu | oil |
| 62 | O-pentyl | 6-Br | Et | solid |
| 63 | OEt | 6-Br | pentyl | solid |
| 64 | OBu | 6-F | Pr | 51–3 |
| 65 | OBu | 6-Br | Me | 105–6 |
| 66 | SCH₂C≡CH | 6-Br | Et | 178–80 |
| 67 | S-benzyl | 6-Br | Et | 103–4 |
| 68 | SBu | 6-Br | Et | 70–1 |
| 69 | SPrⁱ | 6-Br | Et | 107–8 |
| 70 | N(Me)Bu | 6-Br | Et | 78–9 |
| 71 | NHCH₂C≡CH | 6-Br | Et | 209–10 |
| 72 | SH | 6-Br | Pr | 166–7 |
| 73 | SMe | 6-Br | Bu | 81–2 |
| 74 | SMe | 6-Br | Ph | 180–1 |
| 75 | SOMe | 6-Br | Bu | 118–9 |
| 76 | SOMe | 6-Br | Ph | solid |
| 77 | OBu | 6-Me | Pr | 51–2 |
| 78 | NMe₂ | 6-Br | Bu | 88–9 |
| 79 | SO₂Et | 6-Br | Pr | 110–1 |
| 80 | SBu | 6-Br | Ph | 119–20 |
| 81 | SBu | 6-Br | H | 105 |
| 82 | 1-methyl-1,2,4-triazolyl | 6-Br | Pr | 154–5 |
| 83 | SEt | 6-Br | Ph | 151–2 |
| 84 | O-benzyl | 6-Br | Pr | 50–2 |
| 85 | OEt | 6-Me | Pr | solid |
| 86 | SO₂Me | 6-Br | Bu | 130–1 |
| 87 | OEt | 6-Br | Bu | 68–72 |
| 88 | O(CH₂)₂C≡CH | 6-Br | Pr | 69–71 |
| 89 | OBuˢ | 6-Br | Pr | solid |
| 90 | O(CH₂)₂CH=CH₂ | 6-Br | Pr | solid |
| 91 | OBuⁱ | 6-Br | Pr | 53–4 |
| 92 | OBu | 6-OMe | Pr | 52–4 |
| 93 | O-CH₂-(tetrahydrofuran-2-yl) | 6-Br | Pr | solid |
| 94 | OCH₂C≡CH | 6-Br | Pr | 110–2 |
| 95 | OPrⁱ | 6-Br | Pr | 67–8 |
| 96 | OMe | 6-NO₂ | Pr | 139–41 |

-continued

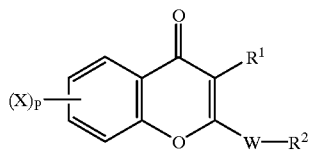

| Cpd | WR² | (X)ₚ | R¹ | m.p. (° C.) |
|---|---|---|---|---|
| 97 | OBu | 7-OMe | Pr | 62–4 |
| 98 | OMe | 6-NH₂ | Pr | 84–6 |
| 99 | SH | 7-OMe | Ph | 216–20 |
| 100 | SMe | 7-OMe | Ph | 136–9 |
| 101 | O-(4Me-benzyl) | 6-Br | Pr | 112–4 |
| 102 | O-(3CF₃-benzyl) | 6-Br | Pr | 75–9 |
| 103 | OMe | 6-Br | H | 169–70 |
| 104 | OMe | 6-SMe | Pr | 72–4 |
| 105 | SMe | 6-Br | H | 120–2 |
| 106 | SCH₂CO₂Et | 7-OMe | Ph | 121–3 |
| 107 | SMe | — | Pr | 59–60 |
| 108 | SMe | 7-OMe | Pr | 108–10 |
| 109 | SCO₂Et | 6-Br | Pr | 142–4 |
| 110 | SMe | 6-Me | H | 102–4 |
| 111 | SCH₂CH₂OMe | 6-Br | Pr | oil |
| 112 | SCH₂CO₂Me | 6-Br | Pr | 138–9 |
| 113 | SMe | 6-Br | Pr | 132–4 |
| 114 | SMe | — | Pr | 107–9 |
| 115 | SMe | 6-Me | Br | 177–8 |
| 116 | S⁻N⁺Bu₄ | 6-Me | Pr | 141–3 |
| 117 | SMe | 6-Br | 2F—Ph | 108–10 |
| 118 | SMe | 6-Br | 3Br—Ph | 156–9 |
| 119 | SMe | 6-Me | Pr | 106–9 |
| 120 | SMe | 7-Me | Pr | 57–8 |
| 121 | OMe | 6-SO₂Me | Pr | 178–9 |
| 122 | OMe | 6-I | Pr | 148–50 |
| 123 | SMe | 6-Br | Et | 160–1 |
| 124 | SBu | 6,7-OCH₂O— | Pr | 58–9 |
| 125 | SO₂Me | 6-Br | H | solid |
| 126 | OMe | 6-Br | CH(OH)Ph | 164–6 |
| 127 | OMe | 6-Br | H | 211–2 |
| 128 | OMe | 6-CN | Pr | solid |
| 129 | SO₂Me | 6-Br | Pr | 144–5 |
| 130 | SMe | — | Et | 130–1 |
| 131 | SO₂Me | 6,7-OCH₂O— | Pr | 179–81 |
| 132 | SMe | 6-Br | 4-ClPh | 205–6 |
| 133 | SH | — | Pr | solid |
| 134 | SMe | — | Pr | solid |
| 135 | SO₂Me | — | Pr | solid |
| 136 | OMe | 6-C≡CSiMe₃ | Pr | solid |
| 137 | SMe | 6,7-CH=CHCH=CH— | Pr | 122–4 |
| 138 | OCH₂CH₂OMe | 6-Br | Pr | 72–4 |
| 139 | SO₂Me | 6-Br | 4-ClPh | 255–60 |
| 140 | OPh | 6-Br | Pr | 90–1 |
| 141 | SPh | 6-Br | Pr | 100–1 |
| 142 | OBu | 6-Me | H | 64–7 |
| 143 | SMe | 6-Br | Buⁱ | 98–100 |
| 144 | SMe | 6-Br | cyclohexyl | 118–20 |
| 145 | OMe | 6-Me | CH=CH₂ | 107–8 |
| 146 | SO₂Me | 6-Br | cyclohexyl | 149–50 |
| 147 | SO₂Me | 6-Br | Buⁱ | 125–6 |
| 148 | O-pentyl | 6-Br | Pr | oil |
| 150 | NHPh | 6-Br | Pr | 120–1 |
| 151 | O-(3-pyridyl) | 6-Br | Pr | 112–3 |
| 152 | ![thiazoline with S-, S, N-Bu] | 6-Br | Pr | 66–8 |
| 153 | OMe | 6-Br | CH=CH—CO₂Me | 205–7 |
| 154 | OMe | 6-Br | CH₂OH | 174–6 |
| 155 | OMe | 6-Br | CH₂OMe | 166–7 |
| 156 | SMe | 6-Cl | Pr | 107–10 |
| 157 | OBu | 6-Br | Buⁱ | 74–6 |
| 158 | OBu | 6-Br | Pr | 68–70 |
| 159 | OBu | 6-CH=CH₂ | Pr | oil |

-continued

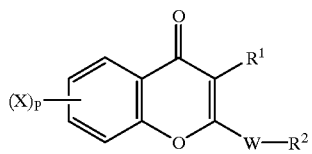

| Cpd | WR² | (X)ₚ | R¹ | m.p. (° C.) |
|---|---|---|---|---|
| 160 | OMe | 6-Br | CH₂OCOMe | 149–50 |
| 161 | OCH₂CH₂Ph | 6-Br | Pr | 89–90 |
| 162 | OBu | 6-Br | cyclohexyl | 73–5 |
| 163 | OMe | 6-Me | 6-(3-Me-5-Me-isoxazoline) | 118–20 |
| 164 | OEt | 6-Br | Pr | 97–99 |
| 165 | OBu | 6-Cl | Pr | 55–6 |
| 166 | OBu | 6-(3-Me-5-Me-isoxazoline) | Pr | 118–20 |
| 167 | SO₂Me | 6,8-Br₂ | Pr | 176–7 |
| 168 | OBu | 6,8-Br₂ | Pr | 99–100 |
| 169 | OCH₂CH₂OMe | 6,8-Br₂ | Pr | 128–9 |
| 170 | OCH₂cyclopropyl | 6,8-Br₂ | Pr | 112–4 |
| 171 | OBu | 5-OH | Pr | oil |
| 172 | OBu | 5-benzyloxy | Pr | oil |
| 173 | SBu | 6-OMe | Pr | 68–70 |
| 174 | O-cyclopentyl | 6-OMe | Pr | oil |
| 175 | NMe₂ | 6-OMe | Pr | oil |
| 176 | OCH₂CH₂OPh | 6,8-Br₂ | Pr | 102–3 |
| 177 | OCH₂SMe | 6-Br | CH₂=CHNOH | 189–90 |
| 178 | SMe | 6-Br | CH₂=CHNOMe | 211–2 |
| 179 | NMe₂ | 6,8-Br₂ | Pr | 115–7 |
| 180 | OBu | 6-Br | CH₂=CHNOMe | 146–7 |
| 181 | OBu | 6-Me | C≡C—SiMe₃ | 92–4 |
| 182 | O-cyclopentyl | 6-Cl | Pr | oil |
| 183 | OBu | 6-Br | CH₂OH | 154–5 |
| 184 | OBu | 6-Br | CH₂OCOMe | 136–7 |
| 185 | SMe | 6-Br | CH=N—O—CH₂—CH=CH₂ | 163–4 |
| 186 | OBu | — | Pr | oil |
| 187 | OBu | 6-Br | CH=N—O—CH₂—CH=CH₂ | 120–1 |
| 188 | SMe | 6-Br | CH(OMe)₂ | 102–4 |
| 189 | SMe | 7-OH | Pr | 192–3 |
| 190 | SMe | 7-O-allyl | Pr | oil |
| 191 | SMe | 7-O—CH₂—C≡CH | Pr | 132–4 |
| 192 | SMe | 7-O—COMe | Pr | 101–3 |
| 193 | SMe | 7-O-(2,4,6-triMeO-pyrimidinyl) | Pr | 108–10 |
| 194 | SMe | 7-O-(4-NO₂—Ph) | Pr | 166–8 |
| 195 | OBu | 6-I | Pr | 69–70 |
| 196 | SMe | 6-OH | Pr | 162–4 |
| 197 | SMe | 6-Obenzyl | Pr | 70–2 |
| 198 | OBu | 6-Obenzyl | Pr | 48–50 |
| 199 | SMe | 6-OMe | Pr | 82–4 |
| 199a | SMe | — | 3-pyridyl | 168–9 |

-continued

| Cpd | WR² | (X)ₚ | R¹ | m.p. (° C.) |
|---|---|---|---|---|
| 199b | (2,4-dichlorophenoxy)methoxymethyl group | 6-Cl | Pr | 127–9 |
| 199c | (diacetone sugar group) | 6-Cl | Pr | oil |
| 199d | SMe | 6-Br | 1,3-dioxolan-2-yl | 177–9 |
| 199e | SO₂Me | 6-OMe | Pr | 153–5 |
| 199f | SMe | 6-OCF₂CF₂Br | Pr | 74–5 |
| 199g | SMe | 7-Ocyclohexyl | Pr | solid |
| 199h | SMe | 6,7-OCH₂O— | Pr | 138–40 |

| Cpd | WR² | (X)ₚ | R¹ | m.p. (° C.) |
|---|---|---|---|---|
| 200 | OH | — | Pr | 210–2 |
| 201 | OBu | 6-Cl | Pr | 48–50 |
| 202 | OBu | 6-Br | Pr | 67–9 |
| 203 | OBu | 6-(4-ClPh) | Pr | 89–90 |
| 204 | O-pentyl | 6-Br | Pr | 55–6 |
| 205 | O—CH₂CH═CMe₂ | 6-Br | Pr | 77–9 |
| 206 | OH | 8-Br | Pr | 192–4 |
| 207 | OH | 6,8-Br₂ | Pr | >250 |
| 208 | OBu | — | Pr | 60–2 |
| 209 | O-(4Br-benzyl) | 6-Br | Pr | 108–10 |
| 210 | O-Allyl | 6-Br | Pr | oil |
| 211 | OCH₂CO₂Me | 6-Br | Pr | 81.5–2.5 |
| 212 | OH | — | Pr | 148–9 |
| 213 | OBu | — | Pr | 40–1 |
| 214 | OBu | — | H | 100–1 |
| 215 | OH | 6-Br | H | 298–300 |
| 216 | O-allyl | 6-Br | H | 156–8 |
| 217 | O-hexyl | 6-Br | Pr | 53–4 |
| 218 | OEt | 6-Br | Pr | 72–3 |
| 219 | OBu | 8-Br | Pr | 48–50 |
| 220 | OBu | 6,8-Br₂ | Pr | solid |
| 221 | OMe | 6-Br | Pr | oil |
| 222 | OCH₂Buⁱ | 6-Br | Pr | solid |
| 223 | OCOBuᵗ | 6-Br | Pr | 167–8 |
| 224 | OCOBu | 6-Br | Pr | 100–1 |
| 225 | OCOMe | 6-Br | Pr | 135–6 |
| 226 | OBu | 6-Br | H | 164–6 |
| 227 | OCOBu | — | Pr | 117–9 |
| 228 | OCOBu | 6-Br | H | 141–2 |

-continued

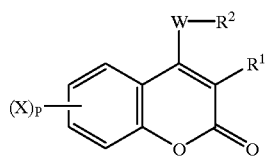

| Cpd | WR² | (X)ₚ | R¹ | m.p. (° C.) |
|---|---|---|---|---|
| 229 | O-cyclopentyl | 6-Br | Pr | solid |
| 230 | O-(2Cl,4F—Ph) | 6-Br | Pr | 122–3.5 |
| 231 | OBu | 5-O-benzyl | Pr | 54–6 |
| 232 | OCH₂CH=CHMe | 6-Br | Pr | oil |
| 233 | —N(H)—cyclohexyl-4-Buᵗ | — | H | 215–8 |
| 234 | OH | 6-Br | Bu | 186–7 |
| 235 | OH | 6-Br | Et | 186–9 |
| 236 | OBu | 6-Br | Et | 35–6 |
| 237 | OEt | 6-Br | pentyl | 53–5 |
| 238 | OBu | 6-Br | Bu | 49.5–50 |
| 239 | O-pentyl | 6-Br | Et | 46–7 |
| 240 | OH | 6-F | Pr | 180–2 |
| 241 | OBu | 6-F | Pr | <40 |
| 242 | OBu | 6-Br | CH=NOMe | 79–80 |
| 243 | OH | 6-Br | Me | 262–3.5 |
| 244 | OBu | 6-Br | Me | 64–66 |
| 245 | OCH₂CO-(4Buᵗ—Ph) | — | H | 194–7 |
| 246 | OBu | 6-Br | CH=NOEt | gum |
| 247 | OBu | 6-Br | CH=NOallyl | oil |
| 248 | OH | 7-Cl | Pr | 165–6 |
| 249 | OCH₂-(4Buᵗ—Ph) | — | H | 172–5 |
| 250 | OBu | 7-Cl | Pr | 35–6 |
| 251 | OCH₂CN | 6-Br | Pr | 97–9 |
| 252 | OCH₂CH₂OPh | 6-Br | Pr | 79–80 |
| 253 | NHPh | 6-Br | Pr | 152–5 |
| 254 | OH | 6-NO₂ | Pr | 228–30 |
| 255 | OSO₂Me | 6-Br | Pr | 132–3 |
| 256 | OCH₂cyclopropyl | 6-Br | Pr | 45–7 |
| 257 | OBu | 6-NO₂ | Pr | oil |
| 258 | O⁻N⁺Bu₄ | 6-Me | Pr | 85–7 |
| 259 | OCH₂Pr | 6-Br | Pr | 121–3 |
| 260 | OH | 6-(4-hydroxy-6-methyl-3-Pr-coumarin) | Pr | 290–3 |
| 261 | OBu | 6-NH₂ | Pr | 82–4 |
| 262 | OEt | 6-Me | Pr | 61–3 |
| 263 | OSO₂-(2,4,6-Me₃Ph) | 6-Br | Pr | 121–3 |
| 264 | O-CH₂-(tetrahydrofuran-2-yl) | 6-Br | Pr | 64–6 |
| 265 | OBuⁱ | 6-Br | Pr | 59–61 |
| 266 | OCH₂CH₂C≡CH | 6-Br | Pr | 72–4 |
| 267 | OBuˢ | 6-Br | Pr | gum |
| 268 | OCH₂CH₂CH=CH₂ | 6-Br | Pr | 52–4 |
| 269 | OBu | 6-I | Pr | 99–100 |
| 270 | OBu | 6-NHCOMe | Pr | 171 |
| 271 | OCH₂C≡CH | 6-Br | Pr | 50–2 |
| 272 | OCH₂CH₂OMe | 6-Br | Pr | 66–8 |
| 272 | OH | 6-OMe | Pr | 188–9 |

-continued

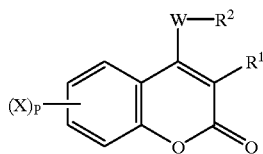

| Cpd | WR² | (X)ₚ | R¹ | m.p. (° C.) |
|---|---|---|---|---|
| 274 | NMe | 6-Br | Pr | 154–6 |
| 275 | SMe | 6-Br | Pr | 108–9.5 |
| 276 | OBu | 6-OMe | Pr | 67–8.5 |
| 277 | OH | 7-OMe | Pr | 194–6 |
| 278 | OPrⁱ | 6-Br | Pr | 47–9 |
| 279 | OCO₂Et | 6-Br | Pr | 91–2 |
| 280 | OMe | 6-NO₂ | Pr | 84 |
| 281 | OMe | 8-NO₂ | Pr | 70–3 |
| 282 | OMe | 6-NH₂ | Pr | 86 |
| 283 | OBu | 7-OMe | Pr | oil |
| 284 | ![epoxyethoxy] | 6-Br | Pr | 75–7 |
| 285 | OCONHEt | 6-Br | Pr | 207–9 |
| 286 | ![glycidyl] | 6-Br | Pr | 91–3 |
| 287 | OCH₂OCOBuᵗ | 6-Br | Pr | 88–90 |
| 288 | O⁻N⁺H₂Bu₂ | 6-Br | Pr | 114–5 |
| 289 | O-(4Me-benzyl) | 6-Br | Pr | 85–7 |
| 290 | ![2,4,6-trichlorophenoxyethoxy] | 6-Br | Pr | 99–101 |
| 291 | O-(3CF₃-benzyl) | 6-Br | Pr | 89–91 |
| 292 | OMe | 6-Br | H | 185–7 |
| 293 | S-(4Cl-benzyl) | 6-Br | Pr | 92–4 |
| 294 | S-(4Buᵗ-benzyl) | — | H | 183–6 |
| 295 | O-(3,5Me₂-Ph) | 6-Br | Pr | 110–2 |
| 296 | OCOPh | 6-Br | Pr | 124–6 |
| 297 | S-benzyl | 6-Br | Pr | 91–2 |
| 298 | S-(4MeO—Ph) | 6-Br | Pr | 80–2 |
| 299 | S-(3,4Cl₂Ph) | 6-Br | Pr | 128–30 |
| 300 | OBu | 6-SO₂Me | Pr | 153–4 |
| 301 | OMe | 6-SO₂Me | Pr | 137–9 |
| 302 | OH | 7-OH | Pr | 172–3 |
| 303 | S-(4MeO-benzyl) | 6-Br | Pr | 91–3 |
| 304 | OH | 6-Br | CH₂NHMe | >200 |
| 305 | OH | 6-Me | H | 258–60 |
| 306 | OBu | 6-Me | H | 110–2 |
| 307 | OBu | 6-Me | Br | 65–7 |
| 308 | OBu | 6-Br | Br | 71–3 |
| 309 | OBu | 6-Me | 3Cl,4F-phenyl | 90–1 |
| 310 | OH | 5-Obenzyl | Pr | solid |
| 311 | OBu | 6-CH₂Br | Br | 135–6 |
| 312 | OBu | 6-Me | 3CF₃-phenyl | 107–9 |
| 313 | OBu | 6-Me | 2-furyl | 54–5 |
| 314 | ![dicyclohexylammonium oxide] | 6-Br | Pr | 166–7 |

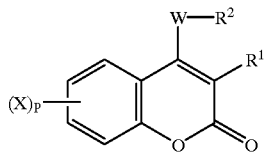

| Cpd | WR² | (X)ₚ | R¹ | m.p. (° C.) |
|---|---|---|---|---|
| 315 | O⁻N⁺HEt₃ | 6-Br | Pr | oil |
| 316 | OBu | 6-Br | CH₂NHMe | 230 dec |
| 317 | OBu | 6-Me | CH=CH₂ | oil |
| 318 | OMe | 6-Br | CH=CHCO₂Me | 195–6 |

Those compounds in the previous Examples for which melting points are not quoted have the following characteristic nmr data Cpd ¹HNMR(CDCl₃)

18 2 rotamers
   0.95(6H, m, 2× CH₃), 1.2–1.65(4H, m, 2× CH₂), 2.0(2H, m, CH₂),
   2.95 and 3.1(3H, s, CH₃), 3.15 and 3.5(2H, m, CH₂),
   4.2–4.4(2H, m, CH₂) 6.9(1H, d, ArH),7.5(1H, dd, ArH), 7.7 and 7.85(1H, d, ArH)

45 1.0 (6H, m, 2× CH₃), 1.4 (2H, m, CH₂), 1.58 (2H, m, CH₂)
   1.7 (2H, m, CH₂), 2.55 (2H, m, CH₂), 3.1 (3H, s, NCH₃)
   3.4 (2H, t, CH₂), 7.18 (1H, d, ArH), 7.6 (1H, dd, ArH)
   8.28 (1H, d, ArH)

58 0.98 (6H, m, 2× CH₃), 1.58 (2H, m, CH₂), 1.7 (2H, m, CH₂)
   2.55 (2H, m, CH₂), 3.1 (3H, s, NCH₃), 3.35 (2H, t, CH₂)
   7.15 (1H, d, ArH), 7.58 (1H, dd, ArH), 8.28 (1H, d, ArH)

61 0.9 (3H, t, CH₃), 1.0 (3H, t, CH₃), 1.25–1.6 (6H, m, 3× CH₂),
   1.8 (2H, m, CH₂), 2.5 (2H, t, CH₂), 4.4 (2H, t, O CH₂),
   7.17 (1H, d, ArH), 7.65 (1H, dd, ArH), 8.3 (1H, d, ArH)

62 0.9 (3H, t, CH₃), 1.1 (3H, t, CH₃), 1.4 (4H, m, 2× CH₂)
   1.8 (2H, m, CH₂), 2.5 (2H, q, CH₂), 4.4 (2H, t, OCH₂)
   7.25 (1H, d, ArH), 7.65 (1H, dd, ArH), 8.35 (1H, d, ArH)

63 0.9 (3H, t, CH₃), 1.4 (3H, t, CH₃), 1.6 (6H, m, 3× CH₂)
   2.6 (2H, t, CH₂), 4.15 (2H, q, OCH₂), 7.25 (1H, d, ArH)
   7.6 (1H, dd, ArH), 7.8 (1H, d, ArH)

76 2.9 (3H, s, SOCH₃), 7.2 (2H, m, 2ArH), 7.4 (3H, m, 3ArH)
   7.6 (1H, d, ArH), 7.8 (1H, dd, ArH), 8.4 (1H, d, ArH)

85 0.82 (3H, t, CH₃), 1.35 (3H, t, CH₃), 1.4 (2H, m, CH₂)
   2.32 (3H, s, ArCH₃), 2.38 (2H, m, CH₂), 4.4 (2H, q, OCH₂)
   7.15 (1H, d, ArH), 7.25 (1H, dd, ArH), 7.9 (1H, d, ArH)

89 0.9 (6H, t, 2× CH₃), 1.35 (3H, d, CH₃), 1.4 (2H, m, CH₂)
   1.7 (2H, m, CH₂), 2.4 (2H, t, CH₂), 4.95 (1H, m, CH)
   7.2 (1H, d, ArH), 7.6 (1H, dd, ArH), 8.25 (1H, d, ArH)

90 0.85 (3H, t, CH₃), 1.4 (2H, m, CH₂), 2.4 (2H, t, CH₂)
   2.5 (2H, m, CH₂), 4.4 (2H, t, CH₂), 5.1 (2H, t, CH₂)
   5.8 (1H, m, CH), 7.15 (1H, d, ArH), 7.6 (1H, dd, ArH)
   8.25 (1H, d, ArH)

93 0.95 (3H, t, CH₃), 1.5 (2H, m, CH₂), 1.7–2.1 (4H, m, 2× CH₂)
   2.5 (2H, t, CH₂), 3.9 (2H, m, CH₂), 4.3 (1H, m, CH), 4.4 (2H, d, OCH₂)
   7.25 (1H, d, ArH), 7.65 (1H, dd, ArH), 8.3 (1H, d, ArH)

111 0.9 (3H, t, CH₃), 1.6 (2H, m, CH₂), 2.6 (2H, m, CH₂), 3.3 (2H, t, CH₂)
   3.4 (3H, s, OCH₃), 3.7 (2H, t, CH₂), 7.3 (1H, m, ArH), 7.7 (1H, m, ArH)
   8.3 (1H, d, ArH)

125 3.52 (3H, s, SO₂CH₃), 7.0 (1H, s, CH), 7.82 (1H, d, ArH)
   8.1 (1H, dd, ArH), 8.18 (1H, d, ArH)

128 1.0 (3H, t, CH₃), 1.5 (2H, m, CH₂), 2.5 (2H, m, CH₂)
   4.1 (3H, s, OCH₃), 7.4 (1H, d, ArH), 7.8 (1H, d, ArH)
   8.5 (1H, s, ArH)

133 1.0 (3H, t, CH₃), 1.6 (2H, m, CH₂), 2.8 (2H, m, CH₂)
   5.2 (2H, s, OCH₂), 6.9 (1H, d, ArH), 7.2 (1H, d, ArH)
   7.4 (6H, s, ArH ×6), 9.9 (1H, bs, SH)

134 1.0 (3H, t, CH₃), 1.5 (2H, m, CH₂), 2.5 (2H, m, CH₂)
   2.6 (3H, s, SCH₃), 5.2 (2H, s, OCH₂), 6.8 (1H, d, ArH)
   6.9 (1H, d, ArH), 7.3 (1H, m, ArH), 7.4 (3H, m, 3× ArH)
   7.6 (2H, d, 2× ArH)

135 1.1 (3H, t, CH₃), 1.6–1.7 (2H, m, CH₂), 2.9 (2H, m, CH₂),
   3.2 (3H, s, SO₂CH₃), 5.2 (2H, s, OCH₂), 6.8 (1H, d, ArH)
   7.1 (1H, d, ArH), 7.3–7.4 (4H, m, 4× ArH), 7.6 (2H, m, 2×ArH)

136 0.3 (9H, s, 3× SiCH₃), 0.9 (3H, t, CH₃), 1.5 (2H, m, CH₂)
   2.5 (2H, m, CH₂), 4.1 (3H, s, OCH₃), 7.3 (1H, m, ArH)
   7.7 (1H, m, ArH), 8.3 (1H, d, ArH)

148 0.8–1.0 (6H, m, 2× CH₃), 1.4–1.9 (8H, m, 4× CH₂), 2.5 (2H, m, CH₂)
   4.4 (2H, m, O CH₂), 7.1 (1H, d, ArH), 7.6 (1H, dd, ArH), 8.3 (1H, d, ArH)

186 0.9 (3H, t, CH₃), 1.03 (3H, t, CH₃), 1.53 (4H, m, 2 × CH₂)
   1.82 (2H, m, CH₂), 2.49 (2H, t, CH₂), 4.44 (2H, t, CH₂)
   7.39 (2H, m, 2× ArH), 7.6 (1H, m, ArH), 8.22 (1H, m, ArH)

171 0.8–1.1 (6H, m, 2× CH₃), 1.3–1.5 (4H, m, 2× CH₂), 1.7–1.9 (2H, m, CH₂)
   2.3 (2H, m, CH₂), 4.4 (2H, t, OCH₂), 6.6 (2H, m, ArH)
   7.4 (1H, t, ArH)

172 0.9–1.1 (6H, m, 2× CH₃), 1.5–1.65 (4H, m, 2× CH₂)
   1.8–1.9 (2H, m, CH₂), 2.5 (2H, m, CH₂), 4.4 (2H, t, OCH₂)

5.3 (2H, s, OCH$_2$Ph), 6.8 (1H, d, ArH), 6.9 (1H, d, ArH)
7.3 (1H, m, ArH), 7.35–7.45 (3H, m, 3× ArH), 7.6 (2H, m, 2× ArH)

74 0.9 (3H, m, CH$_3$), 1.5 (2H, m, CH$_2$), 1.7 (4H, m, 2× CH$_2$),
1.9 (4H, m, 2× CH$_2$), 2.5 (2H, t, CH$_2$), 3.9 (3H, s, O CH$_3$), 5.4 (1H, m, OCH),
7.1 (1H, d, ArH), 7.3 (1H, dd, ArH), 7.6 (1H, d, ArH)

175 0.9 (3H, t, CH$_3$), 1.5 (2H, m, CH$_2$), 2.5 (2H, m, CH$_2$), 3.0 (6H, s, NMe$_2$)
3.9 (3H, s, OCH$_3$), 7.1 (1H, d, ArH), 7.3 (1H, dd, ArH), 7.6 (1H, d, ArH)

182 0.95 (3H, t, CH$_3$), 1.5 (4H, m, 2× CH$_2$), 1.7–1.95 (6H, m, 3× CH$_2$),
2.4(2H, m, CH$_2$), 5.35 (1H, m, CH), 7.26 (1H, d, ArH), 7.5 (1H, dd, ArH),
8.16 (1H, d, ArH)

159 0.98 (3H, t, CH$_3$), 1.0 (3H, t, CH$_3$), 1.54 (4H, m, 2× CH$_2$),
1.8 (2H, m, CH$_2$), 2.5 (2H, t, CH$_2$), 4.4 (2H, t, CH$_2$), 5.32 (1H, d, CH),
5.83 (1H, d, CH), 6.78 (1H, m, CH), 7.32 (1H, d, ArH), 7.63 (1H, dd, ArH), 8.2 (1H, d, ArH)

190 1.0 (3H, t, CH$_3$), 1.5–1.6 (2H, m, CH$_2$)
2.5 (2H, m, CH$_2$), 2.6 (3H, s, SCH$_3$)
4.6 (2H, m, CH$_2$), 5.3–5.5 (2H, m, CH$_2$)
5.9–6.1 (1H, m, CH), 6.7 (1H, d, ArH)
7.0 (1H, dd, ArH), 8.1 (1H, d, ArH)

210 0.85(3H, t, CH$_3$), 1.45(2H, m, CH$_2$), 2,35(2H, m, CH$_2$), 4.4(2H, d, OCH$_2$),
5.2(1H, d, CH), 5.3(1H, d, CH), 5.92(1H, m, CH), 7.0(1H, d, ArH),
7.38(1H, dd, ArH), 7.58(1H, d, ArH)

220 1.0(6H, t, 2× CH$_3$), 1.6(4H, m, 2× CH$_2$), 1.8(2H, m, CH$_2$), 2.6(2H, m, CH$_2$),
4.1 (2H, t, OCH$_2$), 7.6(1H, d, ArH), 7.8(1H, d, ArH)

221 0.8(3H, t, CH$_3$), 1.4–1.5(2H, m, CH$_2$), 2.4(2H, m, CH$_2$), 3.8(3H, s, O CH$_3$),
7.0(1H, d, ArH), 7.4(1H, dd, ArH), 7.6(1H, d, ArH)

222 1.0(9H, m, 3× CH$_3$), 1.6–2.0(3H, m, CH$_2$+CH), 2.6(4H, m, 2× CH$_2$),
4.05(2H, t, CH$_2$), 7.1 (1H, d, ArH), 7.6(1H, dd, ArH), 7.8(1H, d, ArH)

229 1.0(3H, t, CH$_3$), 1.5–2.0(10H, m, CH$_2$×5), 2.6(2H, m, CH$_2$),
4.8(1H, bs, OCH), 7.2(1H, d, ArH), 7.6(1H, dd, ArH), 7.8(1H, d, ArH)

232 1.0(3H, t, CH$_3$), 1.6(2H, m, CH$_2$), 1.7(3H, d, CH$_3$), 2.6(2H, m, CH$_2$)
4.65(2H, d, CH$_2$), 5.8(2H, m, 2× CH), 7.2(1H, d, ArH), 7.58(1H, dd, ArH)
7.78(1H, d, ArH)

246 2 isomers
0.6(6H, t, 2× CH$_3$), 0.85(3H, t, CH$_3$), 1.0–1.2(1 1H, m, CH$_3$+4× CH$_2$),
3.85(2H, q, O CH$_2$oxime), 4.0(6H, m, 2× O CH$_2$+O CH$_2$oxime),
6.25(1H, d, ArH), 7.05(1H, d, ArH), 7.15(1H, dd, ArH), 7.3(1H, d, ArH),
7.5(1H, d, ArH), 7.7(1H, d, ArH), 7.9 (1H, s, CH=NOR) 8.05(1H, s, CH=NOR)

247 2 isomers
0.8(6H, t, 2× CH$_3$), 1.25(4H, m, 2× CH$_2$), 1.45(4H, m, 2× CH$_2$),
4.15(4H, t, 2× O CH$_2$), 4.5(2H, d, OCH$_2$), 4.65(2H, d, OCH$_2$),
5.1 (2H, m, 2× C=CH), 5.25(2H, m, 2× C=CH), 5.75 (1H, m, CCH=C),
6.0(1H, m, CCH=C), 6.45(1H, d, ArH), 7.25(1H, d, ArH),
7.35(1H, dd, ArH), 7.55(1H, d, ArH), 7.7(1H, dd, ArH),
7.95(1H, d, ArH), 8.15(1H, s, CH=NOR), 8.3(1H, s, CH=NOR)

257 1.0(6H, m, 2× CH$_3$), 1.6(4H, m, 2× CH$_2$), 1.9(2H, m, CH$_2$), 2.6(2H, m, CH$_2$)
4.15(2H, t, O CH$_2$), 7.45(1H, d, ArH), 8.35(1H, dd, ArH), 8.6(1H, d, ArH)

267 1.05(6H, m, 2× CH$_3$), 1.3(3H, d, CH$_3$), 1.55–1.95(4H, m, 2× CH$_2$),
2.5(2H, m, CH$_2$), 4.4(1H, m, CH), 7.2(1H, d, ArH), 7.55(1H, dd, ArH),
7.8(1H, d, ArH)

283 1.0(6H, m, 2× CH$_3$), 1.5–1.7(4H, m, 2× CH$_2$), 1.85(2H, m, CH$_2$),
2.55(2H, t, CH$_2$), 4.85(3H, s, O CH$_3$), 4.05(2H, m, CH$_2$), 6.85(2H, m, 2ArH),
7.55(1H, d, ArH)

310 0.9(3H, t, CH$_3$), 1.5(2H, m, CH$_2$), 2.4(2H, m, CH$_2$), 5.2(2H, s, O CH$_2$),
6.9(1H, d, ArH), 7.1 (1H, d, ArH), 7.4–7.5(6H, bs, ArH), 9.7(1H, bs, OH)

315 0.9(3H, t, CH$_3$), 1.2(9H, t, 3× CH$_3$), 1.5(2H, m, CH$_2$), 2.4(2H, m, CH$_2$),
3.0(6H, q, 3× CH$_2$), 7.0(1H, d, ArH), 7.4(1H, dd, ArH), 8.0(1H, d, ArH)

317 1.02(3H, t, CH$_3$), 1.6(2H, m, CH$_2$), 1.9(2H, m, CH$_2$), 2.43(3H, s, Ar CH$_3$),
4.1 (2H, t, O CH$_2$), 5.6(1H, m, CH), 6.4(1H, m, CH), 6.8(1H, m, CH),
7.2(1H, m, ArH), 7.3(1H, dd, ArH), 7.5(1H, d, ArH)

199c 1.9 (3H, t, CH3), 1.3 (6H, d, 2× CH3), 1.5 (6H, d, 2× CH3),
1.6 (2H, m, CH2), 2.4 (2H, m, CH2), 4.1 (1H, m, CH),
4.3 (2H, t, CH2), 4.5–4.8 (3H, m, 3× CH), 5.5 (1H, d, CH),
7.3 (1H, d, ArH), 7.5 (1H, dd, ArH), 8.1 (1H.d, ArH)

199g 1.0 (3H, t, CH3), 1.4–1.65 (8H, m, 4× CH2), 1.7–1.9 (2H, m, CH2),
1.95–2.05 (2H, m, CH2), 2.5 (2H, m, CH2), 2.6 (3H, s, SCH3),
4.3–4.4 (1H, m, OCH), 6.8 (1H, d, ArH), 6.9 (1H, dd, ArH),
8.1 (1H, d, ArH)

Test Example

Compounds are assessed for activity against one or more of the following:

*Phytophthora infestans:* late tomato blight
*Plasmopara viticola:* vine downy mildew
*Erysiphe graminis:* f sp. hordei; barley powdery mildew
*Erysiphe graminis* f. sp. tritici, wheat powdery mildew
*Pyricularia oryzae:* rice blast
*Botrytis cinerea:* grey mould
*Venturia inaequalis:* apple scab
*Leptosphaeria nodorum:* glume blotch
*Pellicularia sasakii:* rice sheath blight Aqueous solutions or dispersions of the compounds at the desired concentration, including a wetting agent, were applied by spray or by drenching the stem base of the test plants, as appropriate. Plants or plant parts were then inoculated with appropriate test pathogens and kept under controlled environment conditions suitable for maintaining plant growth and development of the disease. After an appropriate time, the degree of infection of the affected part of the plant was visually estimated. Compounds are assessed on a score of 1 to 3 where 1 is little or no control, 2 is moderate control and 3 is good to total control. At a concentration of 500 ppm (w/v) or less, the following comounds scored 2 or more against the fungi specified

*Phytophthora infestans*
75,201

*Plasmopara viticola*
12, 24a, 42, 47, 49, 65, 75–6, 82, 92, 107, 118–20, 146–9, 158, 202, 204–5, 213, 217–8, 241–2, 247, 252, 318.

*Erysiphe graminis:* f sp. hordei
12, 14, 41, 42, 44–5, 49–50, 201–2, 204–5

*Erysiphe graminis* f. sp. tritici
2, 5, 6, 11, 23, 26a, 44–5, 47, 49–54, 56–59, 61–64, 66–69, 71, 74–5, 77–9, 82, 84–5, 87–95, 97, 101, 107, 109, 111, 113–4, 116, 119, 122, 124, 129, 136, 138, 143, 145, 148–9, 151–2, 155–62, 216–8, 221–2, 232, 236, 239, 241, 250, 256, 258–9, 261, 265–9, 271–2, 278–9, 283, 289–290, 306, 316.

*Pyricularia oryzae*
56, 69, 71, 73, 79, 86, 106, 114, 251, 316

*Botrytis cinerea*
50, 87, 109, 112, 123, 213, 222, 227, 229, 241, 250, 306.

*Venturia inaequalis*
78, 205, 208, 217, 226, 237, 259.

*Leptosphaeria nodorum*
43, 90, 117, 129, 202, 232, 272, 296

*Pellicularia sasakii*
14, 88, 202

We claim:
1. A compound of the formula

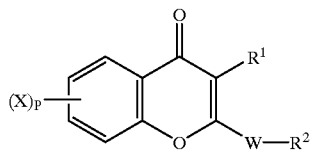

where
W is O, S(O)$_n$, N(R$^3$), N(R$^3$)N(R$^4$), N(R$^3$)O or ON(R$^3$);
R$^1$ is an optionally substituted alkyl, alkenyl, alkynyl, cycloalkyl or phenyl group;
R$^2$, R$^3$ and R$^4$, which may be the same or different, are as defined above for R$^1$, or are acyl or optionally substituted heterocyclyl, and
R$^2$ and R$^3$ or R$^2$ and R$^4$ or R$^3$ and R$^4$ together with the nitrogen or oxygen to which they are attached form an optionally substituted ring which may contain other hetero atoms:
each X, which may be the same as or different from any other X, is halogen, CN, NO$_2$, SF$_5$, B(OH)$_2$, triakylsilyl or a group E, OE or S(O)$_n$E where E is a group as defined hereinbefore for R$^2$ or is optionally substituted amino; or two adjacent groups X together with the atoms to which they are attached form an optionally substituted carbocyclic or heterocyclic ring;
n is 0, 1 or 2;and p is 1 or 2 with one X group being in the 6-position and where p is 2, the other X group is in the 8-position,
with the proviso when WR$^2$ is methoxy, R$^1$ is not 1-methylbenzyl or 1-ethylbenzyl.

2. The compound of claim 1, wherein
X is halogen, alkyl, alkenyl, alkynyl optionally substituted by trialkylsilyl, alkoxy, haloalkoxy, alkenyloxy, alkynyloxy, cycloalkyloxy or alkylthio or two X groups together form a methylenedioxy group;
W is O, S, SO$_2$, NH or N-alkyl;
R$^1$ is optionally substituted alkyl, alkenyl or cycloalkyl; and
R$^2$ is optionally substituted alkyl, cycloalkyl, alkenyl or phenyl.

3. A compound according to claim 2, wherein p is 1, X is halo, W is O, R$^1$ is optionally substituted alkyl, and R$^2$ is optionally substituted alkyl or alkenyl.

4. A compound according to claim 3, wherein X is bromo, R$^1$ is C$_{1-6}$ alkyl, R$^2$ is C$_{1-6}$ alkyl or C$_{2-7}$ alkenyl.

5. A fungicidal composition which comprises a compound as claimed in claim 4 in admixture with an agriculturally acceptable diluent or carrier.

6. A fungicidal composition which comprises a compound as claimed in claim 3 in admixture with an agriculturally acceptable diluent or carrier.

7. A fungicidal composition which comprises a compound as claimed in claim 2 in admixture with an agriculturally acceptable diluent or carrier.

8. A fungicidal composition which comprises a compound as claimed in claim 1 in admixture with an agriculturally acceptable diluent or carrier.

9. A method of combating phytopathogenic fungi at a locus infested or liable to be infested therewith which comprises applying to the locus a compound of formula

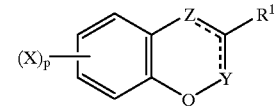

where
one of Z and Y is CO and the other is C—W—R$^2$:
the dotted line indicates a double bond is present in the appropriate position to meet valency requirements;
W is O, S(O)$_n$, N(R$^3$), N(R$^3$)N(R$^4$), N(R$^3$)O or ON(R$^3$);
R$^1$ is an optionally substituted alkyl, alkenyl, alkynyl, cycloalkyl, phenyl, or heterocyclyl group;
R$^2$ is an optionally substituted alkyl, alkenyl, alkynyl, cycloalkyl, phenyl or heterocyclyl group;
R$^3$ and R$^4$, which may be the same or different, are as defined above for R$^1$, or are hydrogen or acyl, or
R$^2$ and R$^3$ or R$^2$ and R$^4$ or R$^3$ and R$^4$ together with the nitrogen or oxygen to which they are attached form an optionally substituted ring which may contain other hetero atoms:
each X, which may be the same as or different from any other X, is halogen, CN, NO$_2$, SF$_5$, B(OH)$_2$, triakylsilyl or a group E, OE or S(O)$_n$,E where E is a group as defined hereinbefore for R$^2$ or is optionally substituted amino; or two adjacent groups X together with the atoms to which they are attached form an optionally substituted carbocyclic or heterocyclic ring;
n is 0, 1 or 2; and
p is 0 to 4;

with the proviso when W is O, $R^2$ is not o-substituted benzyl.

10. The method of claim 9, wherein $R^1$ is an optionally substituted alkyl, alkenyl, alkynyl, cycloalkyl or phenyl group;

$R^3$ and $R^4$, which may be the same or different, are as defined above for $R^1$, or are acyl or optionally substituted heterocyclyl, and p is 1 or 2 with one X group being in the 6-position and where p is 2, the other X group is in the 8-position, with the proviso when $WR^2$ is methoxy, $R^1$ is not 1-methylbenzyl or 1-ethylbenzyl.

11. The method of claim 9, wherein p is 1 or 2;

X is halogen, alkyl, alkenyl, alkynyl optionally substituted by trialkylsilyl, alkoxy, haloalkoxy, alkenyloxy, alkynyloxy, cycloalkyloxy or alkylthio or two X groups together form a methylenedioxy group;

W is O, S, $SO_2$, NH or N-alkyl;

$R^1$ is optionally substituted alkyl, alkenyl or cycloalkyl;

$R^2$ is optionally substituted alkyl, cycloalkyl, alkenyl or phenyl; and in which one X is in the 6-position and the other X when present is in the 8-position.

12. The method of claim 11, wherein p is 1, X is halo, W is O, $R^1$ is optionally substituted alkyl, and $R^2$ is optionally substituted alkyl or alkenyl.

13. The method of claim 12, in which X is bromo, $R^1$ is $C_{1-6}$ alkyl and $R^2$ is $C_{1-6}$ alkyl or $C_{2-7}$ alkenyl.

14. The method according to claim 12, wherein Z is CO.

15. The method according to claim 12, wherein Y is CO.

* * * * *

UNITED STATES PATENT AND TRADEMARK OFFICE
CERTIFICATE OF CORRECTION

PATENT NO : 6,034,121
DATED : March 7, 2000
INVENTOR(S) : Mary Josephine O'MAHONY, et al.

It is certified that error appears in the above identified patent and that said Letters Patent are hereby corrected as shown below.

Title page, item [30] Foreign Priority Date also read:

--October 11, 1996 [PCT] PCT/GB 96/02491--.

Signed and Sealed this

Tenth Day of April, 2001

*Attest:*

NICHOLAS P. GODICI

*Attesting Officer*     Acting Director of the United States Patent and Trademark Office